United States Patent [19]

Larsen et al.

[11] Patent Number: 5,389,524
[45] Date of Patent: Feb. 14, 1995

[54] METHOD AND A SYSTEM FOR QUANTITATIVELY MONITORING A CHEMICAL COMPONENT DISSOLVED IN A LIQUID MEDIUM

[75] Inventors: Bjørn E. H. Larsen; Arne Vinther, both of Køge; Poul Møller, Solrød; Jørn R. Thorsson, Copenhagen; Henrik Søeberg, Albertslund; Jesper L. Sørensen, deceased, late of Roskilde; Lykke B. Larsen, all of Denmark

[73] Assignee: Kemisk Vaerk Koge A/S, Koge, Denmark

[21] Appl. No.: 842,166

[22] PCT Filed: Jul. 30, 1990

[86] PCT No.: PCT/DK90/00196
§ 371 Date: Mar. 24, 1992
§ 102(e) Date: Mar. 24, 1992

[87] PCT Pub. No.: WO91/02254
PCT Pub. Date: Feb. 21, 1991

[30] Foreign Application Priority Data

Jul. 28, 1989 [DK] Denmark .............................. 3748/89

[51] Int. Cl.⁶ ...................... C12Q 1/02; G01N 31/00; G01N 21/00
[52] U.S. Cl. ...................................... 435/29; 435/287; 435/291; 436/3; 436/52; 436/55; 436/808; 422/56; 422/62; 422/82.09; 422/82.05
[58] Field of Search ........................ 435/29, 291, 287; 436/3, 52, 55, 807, 20, 808; 523/205; 422/56, 62, 82.09, 82.05

[56] References Cited

U.S. PATENT DOCUMENTS

| | | | |
|---|---|---|---|
| 4,042,328 | 8/1977 | Seymour | 436/100 |
| 4,159,264 | 6/1979 | Hamilton et al. | 260/155 |
| 4,204,838 | 5/1980 | Atherton et al. | 23/230 |
| 4,440,726 | 4/1984 | Coulson | 436/52 |
| 4,529,703 | 7/1985 | Girling et al. | 436/3 |
| 4,683,212 | 7/1987 | Offenheimer et al. | 436/52 |
| 4,734,354 | 3/1988 | Takagi | 430/249 |
| 4,900,512 | 2/1990 | Meyrat et al. | 436/52 |
| 4,951,669 | 8/1990 | Maxwell et al. | 128/637 |
| 4,997,627 | 3/1991 | BergKuist et al. | 436/52 |
| 5,019,515 | 5/1991 | Gisin et al. | 436/52 |

FOREIGN PATENT DOCUMENTS 0209492 1/1987 European Pat. Off. .
0243310 10/1987 European Pat. Off. .
1517103 7/1978 United Kingdom .

OTHER PUBLICATIONS

Chemical Abstracts, vol. 91, No. 2, Jul. 1979, p. 69.
Kirk-Othmer, Encyclopedia of Chemical Technology, 3rd Edition (1984), Supplement vol., pp. 46–47.
A. Rios et al, "Analytical Potential of Flow-Reversal Injection Analysis", American Chemical Society, 1988, pp. 1540–1545.
Wolf et al., "Concentrative Properties of Aqueous Solutions: Conversion Tables", *CRC Handbook of Chemistry and Physics*, 1973–1974 and 1979.

*Primary Examiner*—Michael G. Wityshyn
*Assistant Examiner*—Louise N. Leary
*Attorney, Agent, or Firm*—Foley & Lardner

[57] ABSTRACT

A method and apparatus for quantitatively monitoring a chemical component dissolved in a liquid medium utilize the creation, in a measurement cell, of an interface zone between the liquid medium and an analytical reagent or reference solution. The concentration or amount of the chemical component are determined by the measurement of a value of a measurement parameter in the interface zone, and the derivation from that value of the concentration or amount of the component in comparison with a baseline or reference value measured for the reagent or reference solution alone. Matrix effects and ghosting errors are avoided. The method and apparatus can be used advantageously for on-line optimization and control of industrial, chemical and biological processes, such as chemical reactions in progress, coupling reactions for the synthesis of azo compounds, and the monitoring of in vivo or in vitro biological systems as well as for conventional analytical purposes.

64 Claims, 14 Drawing Sheets

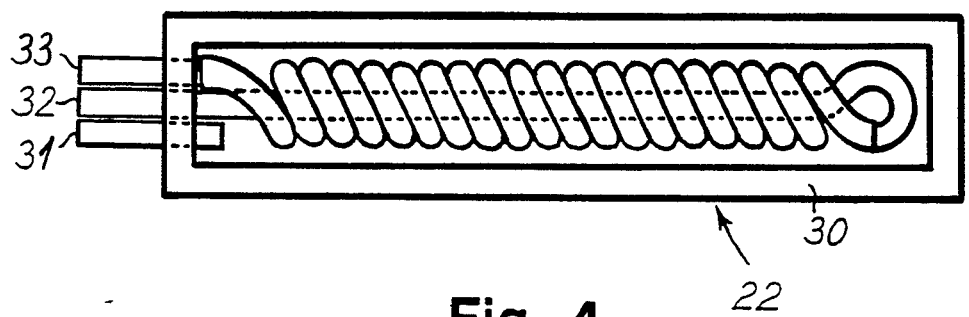
Fig. 4
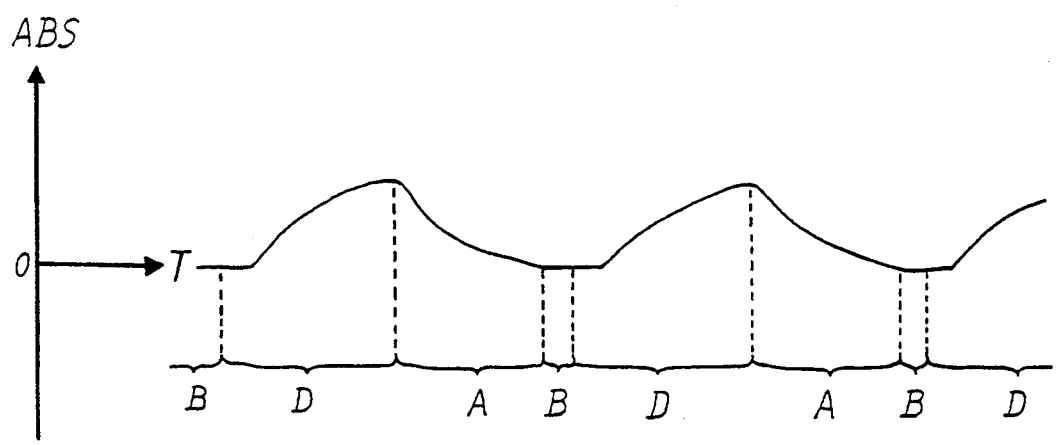
Fig. 5a
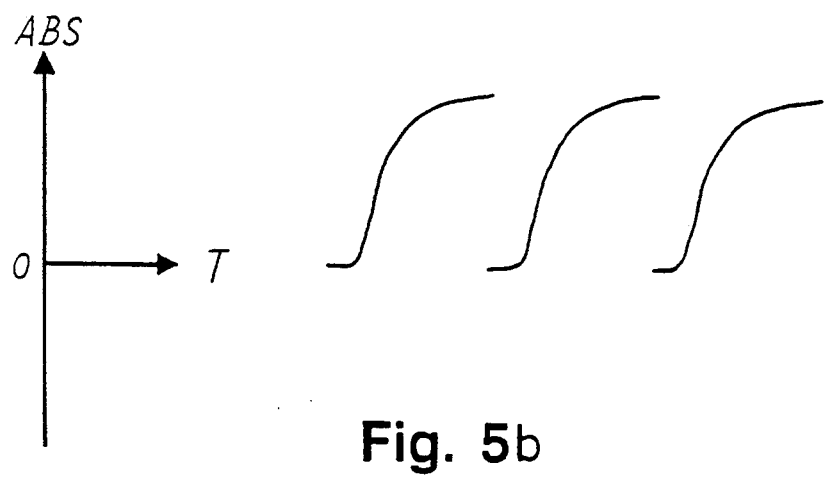
Fig. 5b

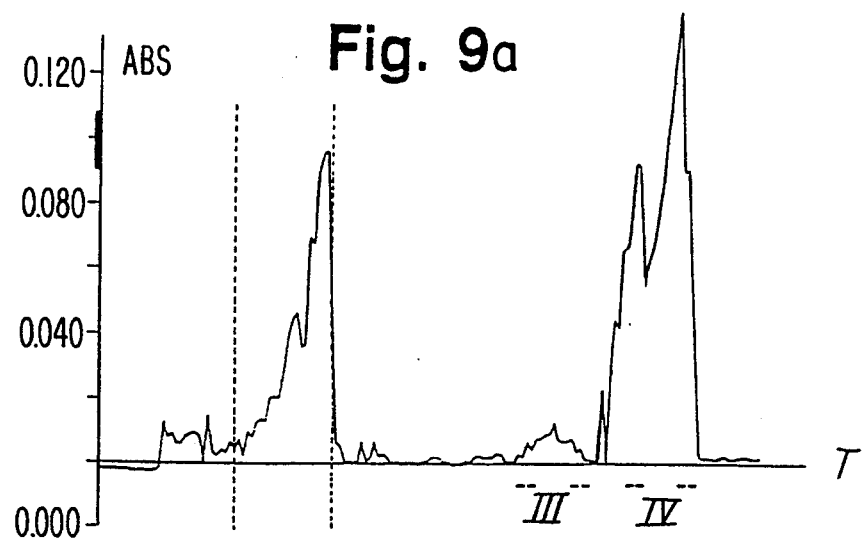
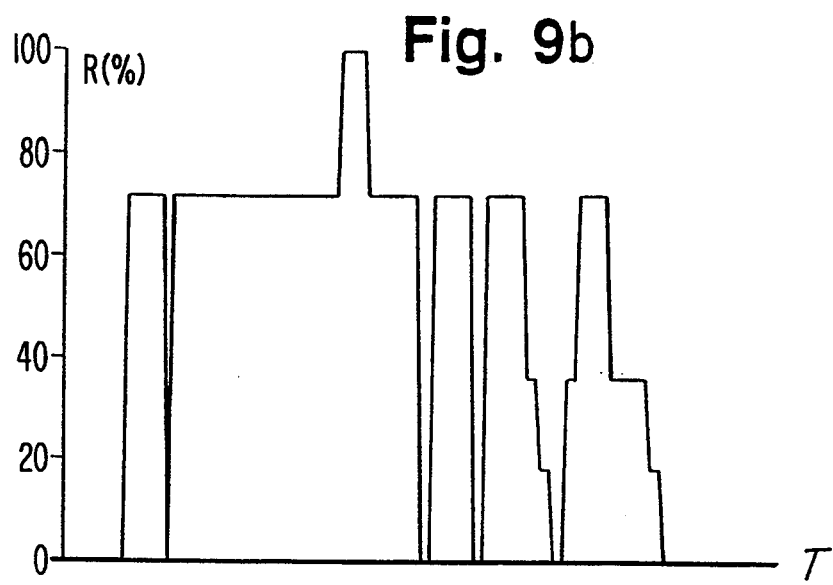
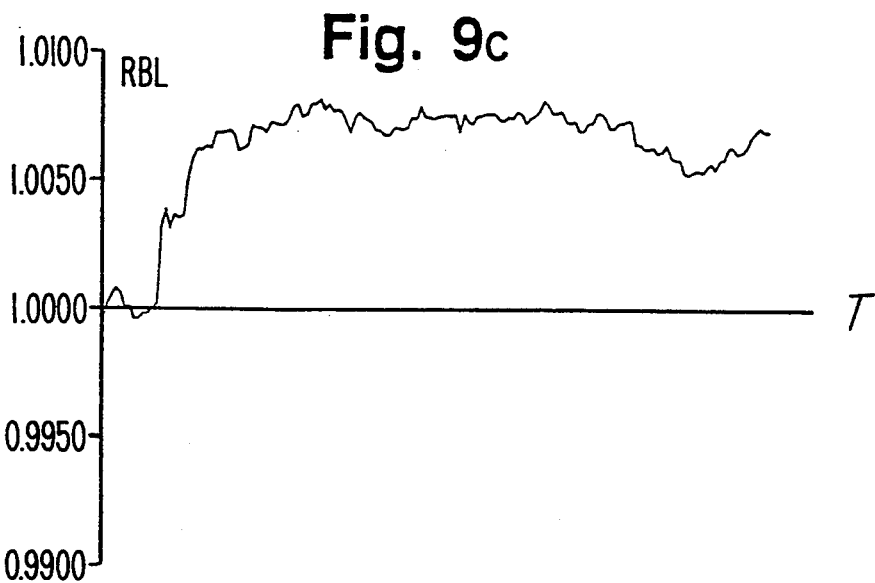

METHOD AND A SYSTEM FOR QUANTITATIVELY MONITORING A CHEMICAL COMPONENT DISSOLVED IN A LIQUID MEDIUM

The present invention relates to a novel method for quantitatively monitoring a chemical component dissolved in a liquid medium, such as a liquid medium for a chemical reaction in progress. The method can be used for on-line optimization and control of industrial chemical and/or biological processes, monitoring of in vivo or in vitro biological systems as well as for conventional analytical purposes.

BACKGROUND OF THE INVENTION

In recent years a great deal of money and effort has been expended on developing automation systems for important industrial processes. However, at present a large number of industrial chemical or biological processes cannot be subjected to process control for various reasons. One of the major reasons is the fact that some processes are extremely difficult or even impossible to monitor in such a way that the information gathered can be used for on-line control of the process, since sensing systems for measuring physical process parameters often do not yield results which adequately reflect the actual state of the process. Hitherto known analytical methods for the monitoring of process parameters are thus generally inadequate. If these processes could be adequately monitored, their optimization would be facilitated, which in turn would result in economic and environmental benefits in the form of, for example, higher yields, energy savings, decreased pollution, etc.

Automation systems necessarily include some kind of device and method for monitoring one or more process parameters so as to obtain relevant and adequate information about the actual state of the system. For on-line control purposes it is essential that the device employed give rapid, reliable and reproducible results, and it should preferably be relatively simple to employ, inexpensive, and constructed in a form which is as compact as possible.

A likely candidate for a method for monitoring in this manner is the analytical method of Flow Injection Analysis (FIA). FIA is based on a combination of the following features: injection of a well-defined volume of sample into a non-segmented, continuously flowing carrier stream of reagent, controlled dispersion of the injected sample zone during its transport from the point of injection to the point of detection, and reproducible timing of all events. In recent years, FIA has developed from an approach for merely rapidly conducting serial assays into a novel concept in solution handling in analytical chemistry and a diagnostic tool to be exploited for general analytical studies. These further developments include a number of variations, for example stopped-flow FIA and flow-reversal FIA. In stopped-flow FIA, the flow is stopped at intervals for an appropriate period of time with the dual purpose of increasing the residence time (which increases the yield of the measured component and thus increases the sensitivity of the measurement) and measuring a reaction rate which serves as the basis for the analytical readout. In flow-reversal FIA, discontinuous passage of the sample plug through the detector in an open flow system is carried out by repeated reversals of the flow; in these reversals, the whole plug is not allowed to pass through the detector, but only a preselected zone of the plug is "sampled", so that the inversion of the cycles takes place within one FIA peak.

Today, traditional FIA, as well as methods developed on the basis thereof, are widely used in analytical laboratories for the automation of wet chemical analyses. Usually, these methods are not applied to process use; however, in a few cases FIA has been used for the monitoring of chemical reaction processes.

The use of FIA for process control purposes is more complicated than its use in the automation of routine laboratory analysis. The complications are particularly associated with the attainment of a sample suited to injection in a FIA system. Withdrawal of a sample from a reaction vessel can give rise to considerable problems such as clogging, change in composition as the result of reaction taking place in the sampling line and delays. It is therefore desirable to avoid the use of sample lines and to use instead equipment which can be introduced directly into the reaction vessel.

An important industrial chemical process which, owing to a lack of adequate monitoring methods, generally speaking is not subjected to on-line process control at present is the process (sometimes known as the azo process) for production of poorly soluble azo pigments, which are a commercially very important class of chemical substances. Azo compounds in general are a class of strongly coloured compounds. They can be intensely yellow, orange, red, blue or green, depending upon the exact structure of the molecule. Due to this property, azo compounds are of tremendous importance as colourants, especially as dyes and pigments.

By the term "colourant" is meant a (usually strongly) coloured chemical compound.

By the term "dye" is meant a colourant which is substantially soluble in the medium in which it is to be used.

By the term "pigment" is meant a colourant which is substantially insoluble in the medium in which it is to be used.

Azo compounds of the general formula Ar—N═N—Ar', where Ar and Ar' independently denote an aromatic group, can be obtained by a coupling reaction in which diazonium salts react with certain aromatic compounds, viz. nucleophilic compounds, in a electrophilic substitution reaction:

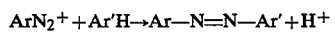

$$ArN_2^+ + Ar'H \rightarrow Ar-N=N-Ar' + H^+$$

The nucleophilic reactant is denoted the coupling component. Suitable coupling components for the formation of azo colourants are aromatic compounds with nucleophilic centres at the aromatic ring, especially naphthols or compounds bearing methylene groups which can undergo enolisation. In a coupling reaction, naphthols react as naphtholates, and the methylene-containing compounds react as enolates.

In order to obtain substantially optimum reaction conditions, pH should be kept constant by the addition of base or buffer, since free acid is formed in the coupling reaction. However, strongly alkaline reaction conditions must be avoided, since the diazonium compound under such conditions reacts to form a trans-diazotate which cannot function as a reactant in a coupling reaction and which decomposes leading to contamination of the reaction mixture. Furthermore, if coupling proceeds too slowly because of unfavourable conditions, phenol formation and/or formation of other undesired products may become the major reactions. In such cases, the phenol formed from the diazonium salt can itself undergo coupling; even a relatively small amount of this undesired coupling product can contaminate the desired material, usually a colourant whose colour should be as pure as possible, to such an extent that the product is worthless. Phenols, naphthols and enols are preferably coupled under mildly acidic to mildly alkaline conditions. Phenols couple fastest in mildly alkaline solutions, and amines couple fastest in mildly acidic solutions. The coupling reaction usually takes place in water.

In the batch-wise production af azo compounds in an industrial process, the actual concentration in the chemical reaction medium of the diazonium reactant which takes part in the coupling reaction is of utmost importance. As is apparent from the above discussion, if the concentration is too high, this may lead to the formation of undesired side products which may discolour the desired product. Furthermore, the formation of undesired side products decreases the actual yield of the reaction, which leads to higher production costs. The rate of reaction also has a significant impact on the degree of (over)saturation of the chemical reaction medium, which in turn influences the crystal size distribution which is in fact obtained. When the production of azo pigments is carried out in a batch-wise manner, the coupling component of the coupling reaction is usually suspended in the liquid reaction medium, and the formed azo pigment, which is only slightly soluble in the reaction medium, will precipitate.

In a continuous process comprising a coupling reaction, one of the most important process conditions is the concentration of diazonium reactant, and it would be a great advantage to be able to maintain this concentration substantially non-fluctuating despite a variation in the rate of introduction of the starting materials. It would also be desirable to be able to control the concentration of diazonium reactant in the reactor outlet, i.e. to maintain the concentration at a chosen value.

Hitherto, the diazonium reactant has most frequently been detected using a spot test in which a coupling component (a reagent) of a coupling reaction is applied to a conventional filter paper. A sample of the reaction medium to be tested is applied to the filter paper at a small distance from the applied sample of coupling component. The sample will spread on the paper and eventually reach the region containing the coupling component (the reagent). If a diazonium compound is present in the sample, a strongly coloured reaction product, an azo compound, will be formed and will be clearly visible (the higher the concentration of diazonium compound, the stronger the colour formed on the filter paper). Besides the very qualitative nature of the test, this detection test is tedious and tiresome and cannot be used for anything but a slow, inaccurate manual control of the addition (or rate of addition) of diazonium reactant to the reactor.

It should be noted that the industrial production of azo compounds generally takes place in reaction vessels having a volume of 40 to 80 $m^3$. This large scale production further emphasizes the need for a fast and reliable method for monitoring.

As a consequence, one object of the invention is to provide a method, preferably a method for utilization in an on-line automation system for optimization and control, which quantitatively monitors a reactant of a coupling reaction in which an azo colourant is formed.

It is essential (i) that the method entails measurements having short response times so that measurement is made on-line or is substantially a real-time measurement with respect to the actual process in the liquid medium, (ii) that the method can be carried out in situ so as to avoid any of the usual disadvantages connected with sampling, and (iii) that the method is suitable for use under a variety of conditions Also, it is most desirable that the method has a high degree of simplicity and that the equipment used in the method can be operated continuously for long periods without requiring maintenance.

In the search for a satisfactory method, it has been found that the well-known FIA methods cannot be applied to the reaction process decribed above for the following reasons:

sampling from a reaction medium comprising liquid and solid phases is extremely difficult, the sample may not be representative of the bulk reaction medium, and any solid phase present in the sample, as is the case in azo pigment production, may lead to blockage of the the sampling system;

the coupling reaction taking place in the reaction medium proceeds in the FIA piping and detection means, thereby leading to precipitation of the azo pigment in question, leading in turn to unreliable analysis results and eventually to blocking of the FIA system;

thus the FIA system is inadequate for monitoring in an on-line automation system, since, at best, very frequent maintenance is essential.

DESCRIPTION OF THE INVENTION

Accordingly, the present invention provides a method for quantitatively monitoring a chemical component dissolved in a liquid medium, and employing a system comprising: a container containing said liquid medium, a measuring cell having a measuring chamber, a reservoir containing an analytical reagent or reference solution, a first conduit connecting said reservoir and said measuring chamber, a second conduit connecting said chamber and said container, and liquid transfer means capable of transferring liquid within said system, said method involving a cycle comprising the following steps in the given relative order:

(i) filling, via said first conduit, said chamber and said second conduit with said reagent or reference solution, (ii) measuring a reference or baseline value for a measurement parameter in the reagent or reference solution present in the measuring chamber, (iii) transferring said liquid medium via the second conduit into the measuring chamber by means of the liquid transfer means, thereby creating an interface zone between the liquid medium and the analytical reagent or reference solution, said interface zone being located within the measuring chamber, (iv) measuring a value for said measurement parameter in the interface zone, the value of said parameter being a function of the amount of said chemical component present in said liquid medium, said measurement optionally being preceded by a period of time necessary for obtaining, within a given thin layer of solution in the interface zone, a substantially uniform composition in a direction perpendicular to the direction of liquid flow in the measuring chamber, and (v) deriving the amount of said chemical component present in the liquid medium on the basis of the measurements made in steps (ii) and (iv).

In a further aspect of the invention, the second conduit is equipped with filter means for retaining suspended solids which may be present in the liquid medium of interest. The filter means may be of any suitable type, e.g. a woven or non-woven fiber filter, such as a glassfiber filter, or a net or mesh filter.

In cases in which the monitoring of the chemical component in question requires that the chemical component itself, or another chemical species whose amount is proportional to the amount of the chemical component in question and which is formed together with said chemical component, reacts with an appropriate analytical reagent before measurement of the parameter in question can take place, it will be necessary that the reservoir contains such an analytical reagent. This will notably be the case when employing an optical parameter, such as transmitted light intensity or absorbance, and when the chemical component in question, or the chemical species whose amount is proportional to the amount of the chemical component in question, does not give rise to satisfactory light absorption; a suitable analytical reagent will then be one which reacts with the chemical component or the chemical species associated with the chemical component so as to give a reaction product whose amount is proportional to the amount of the chemical component and which exhibits satisfactory light absorption at the light wavelength(s) of interest.

A reference solution will be employed in the reservoir in those cases in which the chemical component in question, or a chemical species associated with the chemical component, exhibits properties which permit the direct measurement of the parameter of interest without the requirement of any reaction with an analytical reagent; for example when employing optical means of measuring the parameter, e.g. spectrophotometric means, if the chemical component or an accompanying chemical species exhibits satisfactory light absorption at the wavelength(s) of interest, then no analytical reagent will be necessary and the solution in the resevoir will then be a reference solution.

The liquid transfer means employed in a method according to the invention may be any liquid transfer means, such as a pumping means, suitable for analytical applications, and is preferably such that the direction of pumping or transfer of liquid may be reversed, e.g. a peristaltic pump or a simple piston pump (e.g. a pump of syringe type), preferably a pumping means capable of operation at a variety of substantially constant pumping rates and of being started and stopped repeatedly. In a preferred embodiment of the present invention, the pumping means is a commercially available, electrically driven peristaltic pump.

The interface zone formed between, on the one hand, the liquid medium containing the chemical component in question and, on the other hand, the analytical reagent or reference solution represents the region of local contact and admixture of the two media and, when an analytical reagent solution is employed, is the region in which the analytical reaction occurs; depending inter alia upon the construction of the first and second conduits and the measuring chamber, and upon the rate of liquid transfer or pumping (and the attendant degree of liquid turbulence), the composition within given thin layers of solution on either side of the interface itself will be more or less uniform. A substantially uniform composition within a given thin layer of solution in the interface zone in a direction perpendicular to the direction of flow in the measuring chamber will be particularly important in those cases in which formation of an optically detectable reaction product between the chemical component of interest and an analytical reagent takes place in the interface zone, since inhomogeneities in the concentration of the reaction product and in the liquid matrix in this region (the matrix effect, i.e. an effect deriving from the background medium; vide infra) may yield spurious analytical results. For this reason, and particularly when employing optical, e.g. spectrophotometric, means of detection, it may be important that measurement of the parameter in question first takes place after an interval of time has elapsed after the formation of the interface zone, this interval being sufficient to ensure that a substantially uniform composition is achieved within an above-mentioned, given thin layer of solution in the interface zone as the result of local liquid diffusion.

In a further aspect of the invention, the liquid transfer or pumping means is capable of transferring liquid in a first direction or in a second direction opposite to the first direction and is placed in connection with the first conduit. It is then possible to use one and the same pumping means to transfer both the analytical or reference solution and the liquid medium within the measurement system.

The parameter to be measured in steps (ii) and (iv) may be any parameter which is a function, preferably a simple function such as a linear function, of the concentration of said chemical component in the liquid medium. In a preferred aspect of the method according to the invention, this parameter is an optical or electrochemical parameter. Preferred optical parameters are those conventionally used in the fields of colorimetric, spectrophotometric, fluorimetric, phosphorimetric, turbidimetric/nephelometric or refractometric methods of analysis, especially transmitted light intensity (transmittance), absorbance or refractive index. Preferred electrochemical parameters are those conventionally used in the fields of potentiometric, conductimetric, amperometric, polarographic, voltammetric or coulometric methods of analysis, namely potential, current, resistance and conductivity. Preferred embodiments of an analysis system for use in a method according to the present invention are directed towards the spectrophotometric monitoring of light-absorbing reaction products formed by the reaction of a chemical component of interest with one or more analytical reagents, and the parameter employed is absorbance [i.e. log ($I_o/I$), where $I_o$ is transmitted light intensity with reagent or reference solution, and I is transmitted light intensity with liquid medium and reagent or reagent or reference solution] or a quantity which is a measure thereof.

As mentioned above, notably (but not exclusively) in connection with optical methods of detection, it will be desirable, after the formation of the interface zone, to allow a period of time before measuring the parameter of interest. In preferred aspects of methods according to the present invention, the measurement made in step (iv) is preceded by a period of time required for the disappearance of any matrix effect(s) [also called ghosting error(s)]. As mentioned above, preferred embodiments of an analysis system for use in a method according to the invention employ spectrophotometric detection and measure absorbance or a quantity which is a measure thereof, such as a quantity proportional thereto. As described in greater detail in the Examples (vide infra), the matrix effect of importance in this connection is an effect arising from local variations in refractive index, and failure to take account of this effect can lead to significant errors in the analytical results.

This period required for the disappearance of any matrix effect(s) or ghosting error(s) is suitably a period during which the liquid transfer or pumping means is at a standstill, whereby the liquids in the conduits and in the measuring chamber are substantially at rest such that the diffusion of substances within given thin layers of solution in the interface zone can take place without disturbance from any turbulence due to movement of liquid within the measuring chamber.

As already indicated, one important application of a method according to the present invention is in the monitoring of the level of a reactant participating in a chemical synthesis process, e.g. the synthesis of an azo colourant by a coupling reaction involving a diazonium salt and a second species denoted hereafter by the term "coupling component".

Thus, in a further aspect of a method according to the present invention, the liquid medium is a chemical reaction medium, i.e. a liquid medium in which a chemical reaction takes place. In certain types of chemical synthesis process, such as a process of the above-mentioned type for the synthesis of an azo colourant, it may be desirable or unavoidable that a component participating in the chemical reaction of interest is present in the liquid medium predominantly in undissolved form, and in the case of azo colourant synthesis, the coupling component will often be present in the liquid medium as a solid phase of low solubility in the medium, and from which the coupling component is gradually released into solution.

Thus, in yet another aspect of a method according to the invention, the liquid medium comprises at least one dissolved chemical component and at least one solid chemical component of low solubility dispersed in the liquid medium, the dispersion optionally being achieved by the inclusion, in the liquid medium, of a dispersing agent. Suitable dispersing agents may be chosen from, for example, non-ionic, cationic and anionic detergents. The liquid forming the basis of the liquid medium is preferably a liquid which does not react with any component dissolved or dispersed in the liquid medium; where appropriate, water is often preferable, but other liquids suitable for this purpose may be selected from aromatic hydrocarbons, chlorinated hydrocarbons, glycol ethers, nitriles, esters, alcohols, and dipolar aprotic solvents, including dimethylformamide, dimethylsulfone, tetramethylsulfone and N-methylpyrrolidone. Examples of suitable aromatic hydrocarbons may include benzene, toluene, and o-, m- and p-xylene; examples of suitable chlorinated hydrocarbons may include 1,2-dichloroethane and chlorobenzene; suitable glycol ethers may include ethylene glycol dimethyl ether and propylene glycol dimethyl ether; suitable nitriles may include acetonitrile, propionitrile, butyronitrile and benzonitrile; suitable esters may include methylacetate and ethylacetate; suitable alcohols may include methanol, ethanol, 1-propanol, 2-propanol, 1-butanol, and tert-butyl alcohol.

A chemical reaction to be monitored by a method according to the invention may be a reaction which is carried out in a continuous or batch-wise manner. For example, in the production of an azo colourant, already mentioned, the coupling reaction between a diazonium salt and a coupling component is often performed batch-wise, in aqueous medium (i.e. water is the liquid forming the basis of the liquid medium), by adding a solution of the diazonium salt in question to a stirred dispersion of a fixed quantity of the poorly soluble coupling component, the coupling component being released into solution gradually in the course of the process. Dispersion of the coupling component in this case may be facilitated by the inclusion of a dispersing agent, e.g. a dispersing agent of one of the types mentioned previously. Furthermore, in this process, and in many other types of chemical synthesis process, the reaction product, e.g. an azo compound (azo colourant, notably an azo pigment), precipitates from the reaction medium in the course of the process. Thus, in a further aspect of a method according to the present invention, at least one reaction product of the chemical reaction is a solid which is slightly soluble or substantially insoluble in the liquid medium, and in another aspect this slightly soluble or substantially soluble reaction product is a colourant, preferably an azo compound.

As is apparent from the Examples given herein (vide infra), the ability to continuously and rapidly monitor the concentration of a chosen species renders the Reversing Flow Analysis (RFA) method according to the present invention well-suited to the continuous adjustment of process parameters so as to achieve optimal results, e.g. highest possible yields and/or purity of a chemical synthesis product. Accordingly, the present invention further provides a method for optimization and process control, preferably on-line process control, of an industrial chemical process, this method involving a cycle comprising steps (i) to (v) as described above for a method according to the invention for quantitatively monitoring a chemical component dissolved in a liquid medium, the results of the measurement(s) made in the cycle being used as measured variable(s) in an automation system for regulating one or more controlled variables of the chemical process; in further aspects, the automation system is a closed-loop control system, i.e. an automatic control system employing a measured variable or variables for the automatic regulation of process parameters (controlled variables), and the industrial chemical process may be carried out in a continuous or batch-wise manner. When the industrial chemical process is operated in a continuous manner, the controlled variable(s) of the automation system is/are selected from flow rate of reactant(s) and/or reaction product(s), temperature, pressure, pH, concentration of reactant(s), reaction product(s) or by-product(s), and residence time. When the industrial chemical process is operated batch-wise, the controlled variable(s) of the automation system is/are selected from optimal process time (i.e. the optimal point of termination of said chemical reaction), dosage rate of reactant(s), total amount of reactant(s) added to the liquid medium, concentration of reactant(s), reaction product(s) and by-product(s), volume, temperature, pressure and pH.

A particularly suitable measured variable in connection with the method according to the invention for optimization and process control of industrial chemical processes is the concentration, or a quantity proportional thereto, of a chemical component present in the liquid medium, for example a starting material, an added material, a reaction product or a reaction by-product.

The above-described methods according to the invention are in no way limited to applications to industrial chemical processes; they may, for example, equally well be applied to the monitoring of a chemical component present in the liquid medium employed in a biological process for industrial use. By the term "biological process for industrial use" is meant a process carried out on an industrial scale and involving the intervention of a biological material, e.g. yeasts, bacteria, live or dead cells of plant, animal or human origin and the like, or involving the production of relatively large quantities of a biological material, e.g. a cell-line of bacterial, fungal, plant, animal or human origin. An example is provided by Example 8 described herein (vide infra), which concerns the monitoring of the level of glucose in a fermentor, e.g. in a process vessel in which glucose in low and well-defined concentrations functions as a growth substrate for a microorganism such as a bacterium. Thus, in a further aspect of a method according to the invention as described above involving a biological process for industrial use, the process in question is a microbiological process, such as a fermentation process employing, e.g., a yeast, or a cell culture process.

A further aspect of the invention provides a method for on-line optimization and control of synthesis of azo compounds, wherein a reactant of a coupling reaction taking place in a chemical reaction medium is quantitatively monitored by measuring, in a measuring cell having a measuring chamber and equipped with a light source permanently emitting light, the light absorption of a soluble, coloured reaction product formed by reaction of said reactant in solution with a suitable analytical reagent in solution, the method employing a system comprising:

a container containing said liquid medium, said measuring cell, a reservoir containing an analytical reagent solution, a first conduit connecting said reservoir and said measuring chamber, a second conduit equipped with filter means for retaining suspended solids present in said liquid medium and connecting said measuring chamber and said liquid medium, and liquid transfer means capable of transferring liquid within said system, said method involving a cycle comprising the following steps in the given relative order:

(i) filling, via said first conduit, said chamber and said second conduit with said analytical reagent solution, (ii) measuring a reference or baseline measure of the absorbance in the analytical reagent solution present in the measuring chamber by transmitting a light beam emitted from a light source such as a light-emitting diode (LED) through said reagent solution, said light beam eventually impinging upon a detector, such as a photodiode, so as to generate a signal whose magnitude is related to the value of the absorbance in said analytical reagent solution, (iii) transferring said liquid medium via the second conduit into the measuring chamber by means of the liquid transfer means, thereby creating an interface zone between the liquid medium and the analytical reagent solution, the interface zone being located within the measuring chamber, (iv) measuring a measure of the absorbance in the interface zone by transmitting said light beam emitted from said light source through said liquid medium, said interface zone and said reagent solution present in the measuring chamber, said light beam being emitted in a direction substantially perpendicular to said interface zone and, after passage through said interface zone, eventually impinging upon said detector so as to generate a signal whose magnitude is related to the value of the absorbance in the interface zone, said measurement optionally being preceded by a period of time necessary for obtaining, within a given thin layer of solution in the interface zone, a substantially uniform composition in a direction perpendicular to the direction of liquid flow in the measuring chamber, (v) deriving a value for a measure of the concentration of said reactant in said chemical reaction medium on the basis of the measurements made in steps (ii) and (iv), and, in those cases where said value is outside preselected limits, regulating a process parameter or controlled variable so as bring said value within said preselected limits.

The liquid transfer means may suitably be a means (such as a pumping means) as described earlier, above, and in a preferred aspect of the method, the liquid transfer means is capable of transferring liquid in a first direction or in a second direction opposite to said first direction and is placed in connection with the first conduit.

The analytical reagent solution for use in such a method will normally be an aqueous, i.e. water-based, solution.

In further preferred aspects of such a method, the reactant of the coupling reaction (which preferably takes place in aqueous medium) is a diazonium salt, preferably a diazonium salt in solution or suspension, or is a coupling component of an azo coupling reaction. In a further aspect of such a method, the pH at which the coupling reaction is carried out is in the range 2–12, and the temperature is in the range of from $-5°$ C. to 99° C., preferably from $-5°$ C. to 70° C., more preferably 0°–60° C., especially 0°–50° C., and in a preferred aspect of a coupling reaction taking place under conditions within these limits, the coupling product is a yellow arylide or diarylide pigment (i.e. a pigment derived from an acetoacetanilide as coupling component) and the coupling reaction is carried out at a substantially constant pH in the range 4–6.

In a preferred aspect of a method according to the invention for on-line optimization and control of synthesis of azo compounds, the coupling component in the coupling reaction taking place in the liquid medium (in this case preferably an aqueous medium) is selected from the group consisting of:

substituted and unsubstituted acetoacetanilides, including acetoacet-4-methyl-anilide, acetoacet-2-methyl-4-chloro-anilide, acetoacet-4-chloro-2,5-dimethoxy-anilide, 4-acetoacetylamino-benzenesulfonic acid, acetoacet-2-methyl-anilide, acetoacet-4-methoxy-anilide, acetoacet-2-chloro-anilide, acetoacet-2,4-dimethyl-anilide and acetoacet-2-methoxy-anilide;

naphthol-AS and derivatives thereof, including N-phenyl-3-hydroxy-2-naphthalenecarboxamide (=naphthol-AS), N-(methylphenyl)-3-hydroxy-2-naphthalenecarboxamide and N-(nitrophenyl)-3-hydroxy-2-naphthalenecarboxamide;

$\beta$-naphthol and substituted $\beta$-naphthols, including mono- and dihydroxynaphthalenesulfonic acids and mono- and dihydroxynaphthalenedisulfonic acids;

$\beta$-oxo-naphthoic acid and substituted $\beta$-oxo-naphthoic acids; and 5-pyrazolone and substituted 5-pyrazolones, including 3-methyl-1-phenyl-5-pyrazolone, 3-methyl-1-(4-methylphenyl)-5-pyrazolone, 3-methyl-1-(4-sulfophenyl)-5-pyrazolone and 3-carbethoxy-1-phenyl-5-pyrazolone;

and the diazonium compound of the coupling reaction is obtained by diazotisation of an aromatic amine or diamine selected from the group consisting of: substituted anilines, including 2,4,5-trichloroaniline, 4-methoxy-2-nitroaniline, 4-chloroaniline-3-sulfonic acid, 4-ethoxyaniline-2-sulfonic acid, 2-nitroaniline-4-sulfonic acid, 2-amino-5-chloro-4-ethylbenzenesulfonic acid, 2-methyl-5-nitroaniline, 4-chloro-5-methylaniline-2-sulfonic acid, 4-methylaniline-2-sulfonic acid, 2-methoxy-4-nitroaniline, 4-chloro-4-nitroaniline, 2,4-dinitroaniline, 2,5-dichloroaniline, 5-chloro-4-methylaniline-2-sulfonic acid and 4-aminobenzenesulfonic acid; and substituted benzidines, including 3,3'-dichlorobenzidine, 3,3'-dimethoxybenzidine, benzidine-2,2'-disulfonic acid, 3,3'-dimethylbenzidine and 3,3', 5,5'-tetrachlorobenzidine.

In a further preferred aspect, the analytical reagent solution is an aqueous solution and comprises a buffer and/or an organic solvent. The nature of a buffer which is to be employed in such a method will, of course, depend upon the nature of the species participating in the analytical reaction employed. Suitable buffers are generally to be found amongst phosphates, e.g. $NaH_2PO_4$, $Na_2HPO_4$; citrates, acetic acid/acetate, $NH_4^+/NH_3$ and $NaHCO_3$. Suitable organic solvents will generally be incorporated so as to improve the solubility characteristics of the reaction product formed in the analytical reaction; in the case of measurements employing aqueous media, suitable solvents will be water-miscible solvents such as acetone, N,N-dimethylformamide, tetrahydrofuran, dimethylsulfone or dimethylsulfoxide, and alcohols such as ethanol, 1-propanol, 2-propanol or tert-butyl alcohol.

In preferred aspects of methods according to the invention for on-line optimization and control of synthesis of azo compounds in which the species monitored in the analytical reaction is a diazonium reactant of a coupling reaction taking place in the liquid medium or is a coupling component of such a coupling reaction, in the former case the analytical reagent solution comprises a coupling component (which may or may not be identical with the coupling component employed in the process taking place in the liquid medium) and which bears sulfonic acid, amino and/or hydroxy groups capable of increasing the solubility of the reaction product, i.e. an azo colourant, formed in the analytical reaction; a suitable coupling component for the analytical reagent solution is then preferablu selected from the group consisting of 7-hydroxy-1,3-naphthalenedisulfonic acid, 1,8-dihydroxy-3,6-naphthalenedisulfonic acid and 4-acetoacetylaminobenzenesulfonic acid. When the species monitored is a coupling component of a coupling reaction taking place in the liquid medium, the analytical reagent solution preferably comprises a diazotized aromatic amine bearing sulfonic acid and/or hydroxy groups capable of increasing the solubility of the reaction product, i.e. an azo colourant, formed in the analytical reaction; a suitable diazotized aromatic amine for the analytical reagent solution is then preferably selected from the group consisting of diazotized 4-aminobenzenesulfonic acid, diazotized 3-amino-4-methoxybenzenesulfonic acid, diazotized 3-amino-6-methoxybenzene-sulfonic acid and diazotized 2-amino-5-naphthalenesulfonic acid. Furthermore, when the species monitored is a coupling component which, besides being capable of coupling with a diazonium salt, is capable of forming light-absorbing complexes with a metal ion, e.g. $Fe^{3+}$, then the analytical reagent solution may suitably comprise such a metal ion. In such a case, it is preferred that the analytical reagent solution comprises ferric ions, and that the coupling component is capable of forming complexes with the ferric ions; it is further preferred in this case that the coupling component is an unsubstituted or a substituted acetoacetanilide.

The methods of the present invention differ from the prior art Flow Injection Analysis (FIA) method by measuring the concentration of a chemical substance in a preselected period of time by placing the interface zone in the measuring chamber and measuring a (variable) parameter of the chemical substance by means of a detecting device capable of detecting the parameter in question. In contrast hereto, in traditional FIA the analytical measurement is conducted with a preselected quantity of sample.

A further aspect of the present invention provides a system for quantitatively monitoring a chemical component dissolved in a liquid medium, the system comprising:

a container containing said liquid medium, a measuring or flow cell having a measuring chamber, a reservoir containing an analytical reagent or reference solution, a first conduit connecting said reservoir and said measuring chamber, a second conduit connecting said measuring chamber and said container, liquid transfer means for transferring liquid within said system, and control means connected to said measuring chamber for receiving and processing measuring signals therefrom and connected to said liquid transfer means for controlling the operation thereof, for performing a cycle of operations comprising the following steps in the given relative order:

(i) filling, via said first conduit, said chamber and said second conduit with said reagent or reference solution, (ii) measuring a reference or baseline value for a measurement parameter in the reagent or reference solution present in the measuring chamber, (iii) transferring said liquid medium via the second conduit into the measuring chamber by means of the liquid transfer means, thereby creating an interface zone between the liquid medium and the analytical reagent or reference solution, said interface zone being located within the measuring chamber, (iv) measuring a value for said measurement parameter in the interface zone, the value of said parameter being a function of the amount of said chemical component present in said liquid medium, said measurement optionally being preceded by a period of time necessary for obtaining, within a given thin layer of solution in the interface zone, a substantially uniform composition in a direction perpendicular to the direction of liquid flow in the measuring chamber, and (v) deriving the amount of said chemical component present in the liquid medium on the basis of the measurements made in steps (ii) and (iv).

The invention further relates to a system for on-line optimization and control of synthesis of azo compounds, with which system a reactant of a coupling reaction taking place in a chemical reaction medium is quantitatively monitored by the measurement, employing a measuring cell having a measuring chamber and equipped with a light source permanently emitting light, of the light absorption of a soluble, coloured reaction product formed by reaction of said reactant in solution with a suitable analytical reagent in solution, the system comprising:

a container containing said liquid medium, said measuring cell, a reservoir containing an analytical reagent solution, a first conduit connecting said reservoir and said measuring chamber, a second conduit equipped with filter means for retaining suspended solids present in said liquid medium and connecting said measuring chamber and said liquid medium, liquid transfer means capable of transferring liquid within said system, and control means connected to said measuring chamber for receiving and processing measuring signals therefrom and connected to said liquid transfer means for controlling the operation thereof, said control means having comparator means for comparing the value of a measure of the concentration of said reactant, derived by said signal processing, with a preselected threshold value or values of said measure, and further having threshold means for generating, in those cases where said value is outside the preselected limits, a signal leading to the regulation of a process parameter so as to bring said value within said preselected limits, for performing a cycle of operations comprising the following steps in the given relative order:

(i) filling, via said first conduit, said chamber and said second conduit with said analytical reagent solution, (ii) measuring a reference or baseline measure of the absorbance in the analytical reagent solution present in the measuring chamber by transmitting a light beam emitted from a light source such as a light-emitting diode (LED) through said reagent solution, said light beam eventually impinging upon a detector, such as a photodiode, so as to generate a signal whose magnitude is related to the value of the absorbance in said analytical reagent solution, (iii) transferring said liquid medium via the second conduit into the measuring chamber by means of the liquid transfer means, thereby creating an interface zone between the liquid medium and the analytical reagent solution, the interface zone being located within the measuring chamber, (iv) measuring a measure of the absorbance in the interface zone by transmitting said light beam emitted from said light source through said liquid medium, said interface zone and said reagent solution present in the measuring chamber, said light beam emitted in a direction substantially perpendicular to said interface zone and, after passage through said interface zone, eventually impinging upon said detector so as to generate a signal whose magnitude is related to the value of the absorbance in the interface zone, said measurement optionally being preceded by a period of time necessary for obtaining, within a given thin layer of solution in the interface zone, a substantially uniform composition in a direction perpendicular to the direction of liquid flow in the measuring chamber, (v) deriving a value for a measure of the concentration of said reactant in said chemical reaction medium on the basis of the measurements made in steps (ii) and (iv), and, in those cases where said value is outside preselected limits, regulating a process parameter or controlled variable so as bring said value within said preselected limits.

The control means in a system according to the invention may suitably be CPU (Central Processing Unit) such as a computer which, via the installation of appropriate software, can process signals received from the measuring chamber and, where appropriate, generate a signal for regulating the operation of the liquid transfer means. Such a CPU will often suitably be provided with interfacing means [such as an AD (analog-digital) converter at the signal input side and a DA (digital-analog) converter (where appropriate) at the signal output side] for transforming incoming analog (input) signals to digital signals suitable for processing, and, where relevant, transforming outgoing, generated digital signals to analog signals suitable for regulating the operation of, e.g., a pump.

Such systems according to the invention may further embody any of the features disclosed and discussed above in connection with the related methods according to the invention for quantitatively monitoring a chemical component dissolved in a liquid medium, for optimization or process control, or for on-line optimization and control of synthesis of azo compounds, and the systems according to the invention are well-suited for use in the associated methods according to the invention.

BRIEF DESCRIPTION OF THE DRAWINGS

The drawing consists of 26 figures among which

FIG. 4 is a perspective view of a degasser (22) by means of which analytical or reagent solution may be degassed before it enters the measuring chamber of a measuring cell.

FIG. 5a is a graphical representation (vertical axis: absorbance; horizontal axis: time) of RFA signals obtained when the sample and analytical reagent/reference solution differ only in absorbance (see Example 2).

FIG. 5b is a graphical representation (vertical axis: absorbance; horizontal axis: time) of RFA signal from period D (cf. Example 1) containing the analytical information (see Example 2).

FIG. 9a is a graphical representation (vertical axis: absorbance; horizontal axis: time) of the date from the monitoring of the diazonium salt concentration during the production of Pigment Yellow 1 (see Example 6).

FIG. 9b is a graphical representation (vertical axis: Relative addition rate; horizontal axis: time) of the relative addition rate of diazonium salt solution during the production of Pigment Yellow 1 (see Example 6).

FIG. 9c is a graphical representation (vertical axis: Relative baseline; horizontal axis: time) of the variation of the baseline during the production of Pigment Yellow 1 (see Example 6).—;

FIG: 10b is a graphical representation (vertical axis: Relative addition rate; horizontal axis: time) of the relative addition rate of bis(diazonium) salt solution during the production of Pigment Yellow 13 (see Example 7).

FIG: 10c is a graphical representation (vertical axis: Relative baseline; horizontal axis: time) of the variation of the baseline during the production of Pigment Yellow 13 (see Example 7.)—.

Figure 11:
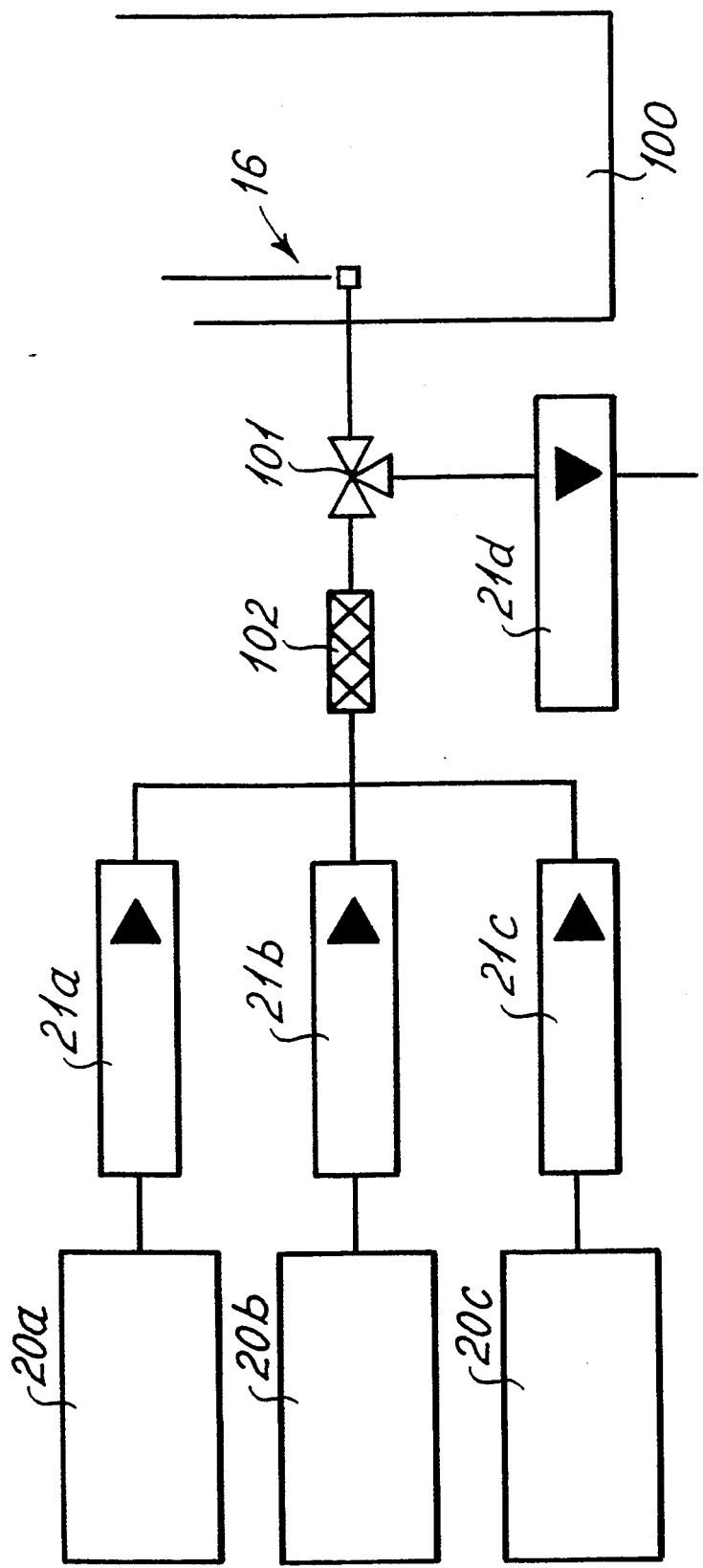

FIG. 11 is a schematic view of a Reversing Flow Analysis system according to the invention for the measurement of glucose in a fermentor (see Example 8).

Figure 12:
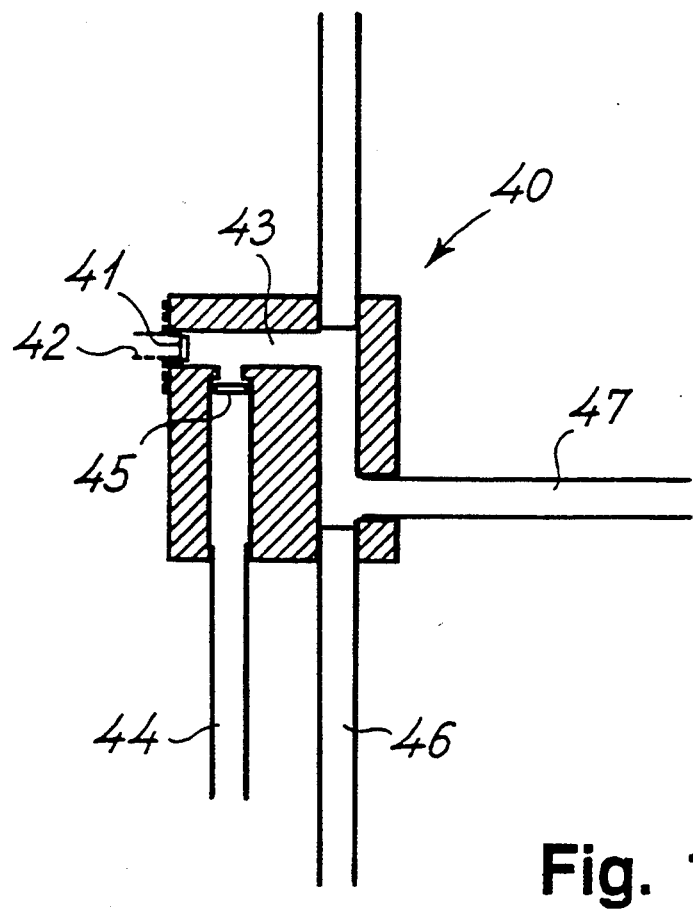

FIG. 12 is a sectional view of an alternative embodiment of a measuring cell for clinical use (see Example 9).

The invention is further illustrated with reference to the drawing and the examples given below.

EXAMPLE 1

An apparatus for use in a method of the invention

Figure 1:
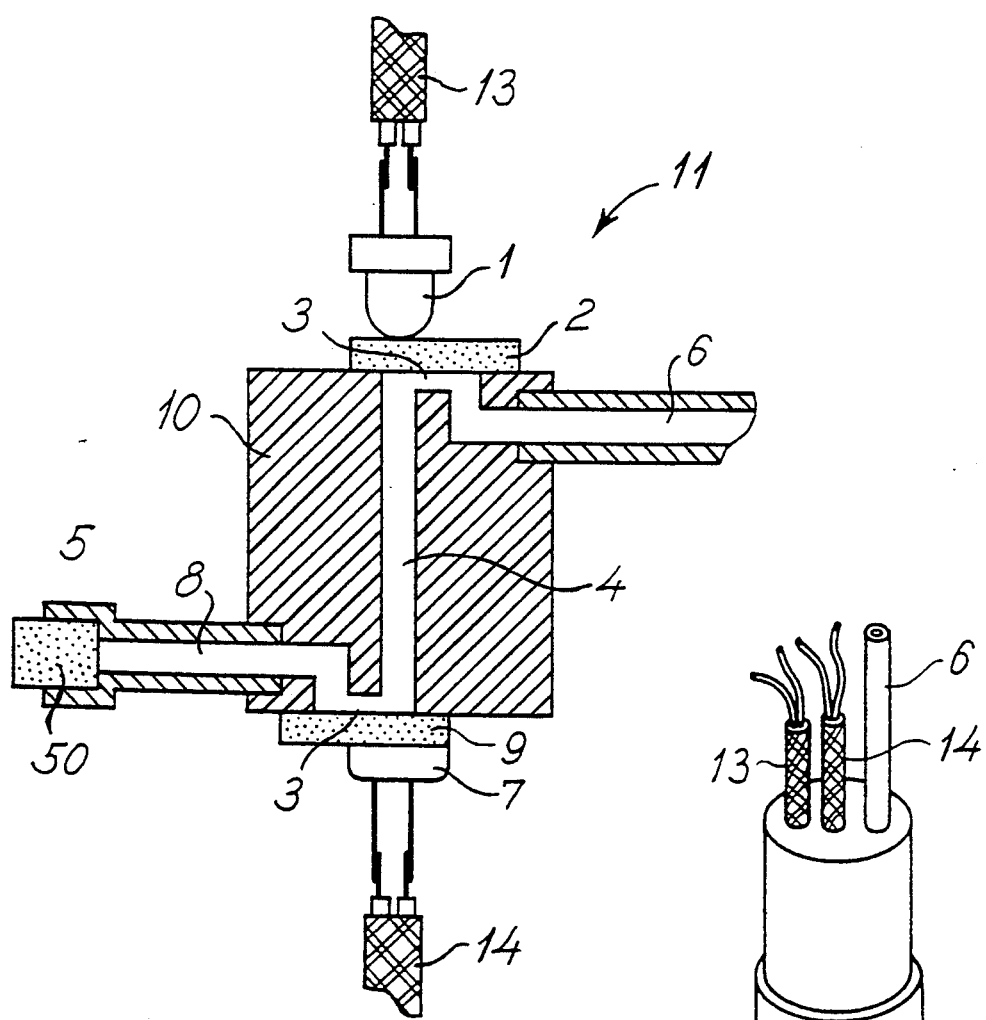
FIG. 1 is a sectional view of a measuring cell or flow cell (11) for spectrophotometric measurements, the flow cell (11) being part of an analysis system of the invention.

In FIG. 1, a measuring cell or flow cell 11 comprises a stainless steel block 10 encompassing a drilled channel 4 (constituting a measuring chamber) having an internal diameter (i.d.) of 0.5 mm (in one embodiment of the invention), 0.7 mm (in a second embodiment) or 0.8 mm (in a third embodiment) and having a length giving an optical path length of 6 mm in the case of i.d. 0.5 mm and 0.8 mm, and 11.4 mm in the case of i.d. 0.7 mm, the drilled channel being a part of the flow path which further comprises milled grooves 3, a first conduit 6 and a second conduit 8, the milled grooves 3 being covered by glass plates (microscope slides) 2 and 9, a light-emitting diode (LED) 1 being placed on the glass plate 2 and a photodiode 7 being placed on the glass plate 9, and a filter 50 being placed in an enlarged extension 5 of the second conduit 8.

The light-emitting diode, the photodiode and the glass plates are fixed in position and attached to the appropriate surfaces of the stainless steel block by means of epoxy glue (Araldit TM) (not shown).

The entire surface of the measuring or flow cell 11, including the upper and lower surfaces bearing the LED and the photodiode, respectively, is sealed with epoxy glue (Araldit TM).

Although the measuring chamber in measuring cells described herein is of circular cross-section, other cross-sectional forms, e.g. square, can equally well be envisaged.

Figure 2:
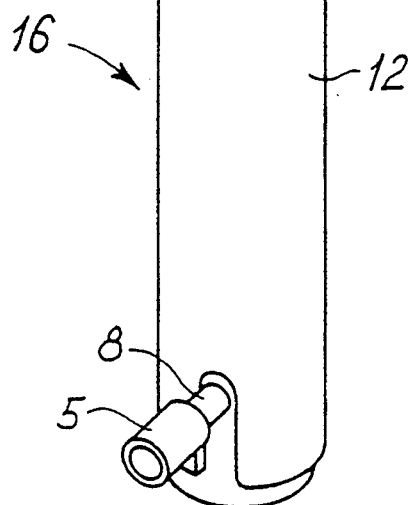
FIG. 2 is a perspective view of a measuring device (measuring and sampling probe) (16) comprising the flow cell enclosed in a stainless steel tube (12) and with connecting electrical contact wires and conduits.

FIG. 2 is a perspective view of a measuring device 16 comprising a measuring or flow cell (not visible) enclosed in a stainless steel tube 12 having an internal diameter of 1.2 cm. Electrical contact wires 13 connect the LED to a power source (shown in FIG. 3b), and electrical contact wires 14 connect the photodiode to an amplifier (shown in FIG. 3a). A first conduit 6 connects the cell and a reservoir of reagent or reference solution. A second conduit 8 connects the cell and a liquid medium. The second conduit 8 has an enlarged section 5 of cylindrical shape with an inner diameter of 1.65 mm and a length of 3.0 mm. This section 5 is completely filled with a cylindrical plug (not shown) made of a porous polymer material (Vyon ®) which serves as a filter. The lower end and lateral opening of the stainless steel tube 12 are sealed with epoxy glue (Araldit TM).

Figure 3:
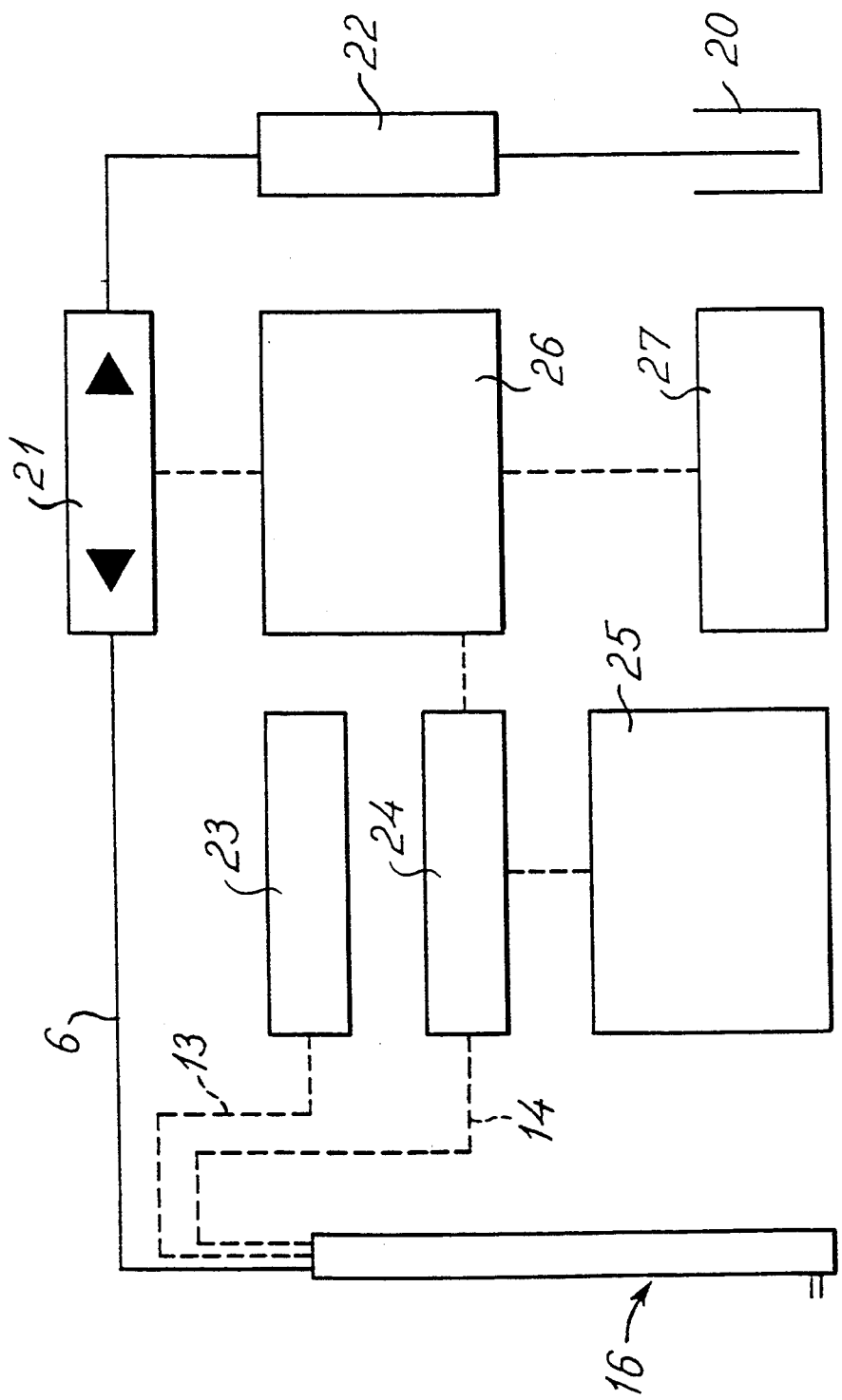
FIG. 3 is a schematic view of a prototype implementation of a measuring and sampling system constituting a presently preferred embodiment of the system according to the invention.

FIG. 3 is a schematic view of a measuring and sampling system as used in Examples 2–7. The conduit 6 is made of Teflon ® and connects the flow cell and a reagent solution reservoir 20 via a peristaltic pump 21 (Alitea C-4 with 8 rollers; Ventur Tekniska AB, Sweden) equipped with a PVC tube and a so-called degasser 22 capable of degassing the reagent solution. Electrical connecting wires 13 connects a power source 23 and the LED of the flow cell. Electrical connecting wires 14 connect the photodiode of the flow cell and an amplifier 24 (see FIG. 3a) which in turn is connected to a pen recorder 25 (Beckman, model 1005) and a computer 26 (BBC Microcomputer). The rotation speed of the peristaltic pump 21 is controlled by the computer 26. For this purpose, an electrical control circuit of the pump 21 is connected to a digital output port of the computer. The direction of rotation as well as the rotation speed is preselected. The rotation speed can be selected among four different settings including stop, and is maintained essentially constant.

Figure 3A:
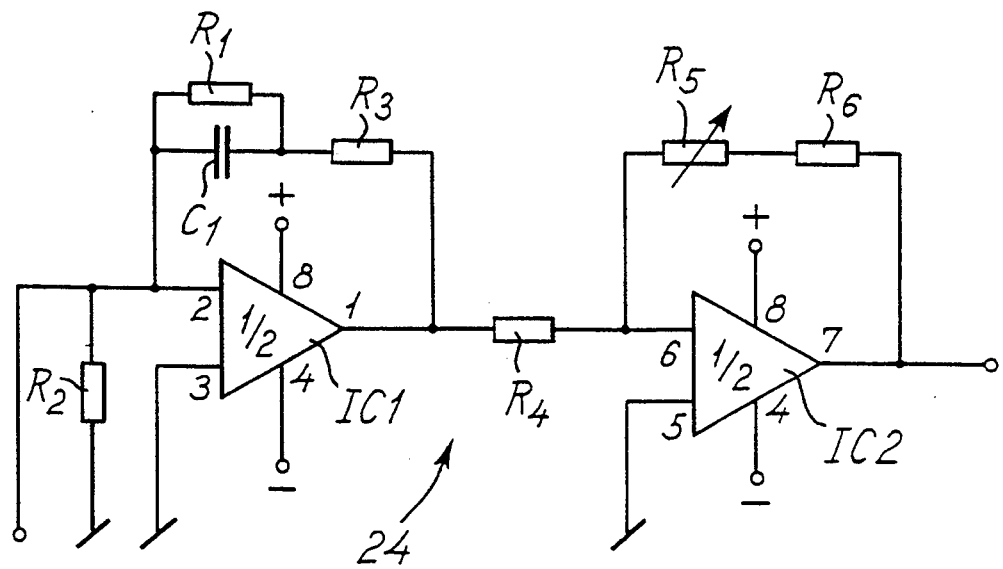
FIG. 3a is a detailed diagrammatic view of a presently preferred implementation or embodiment of an electronic amplifier constituting a component of the prototype implementation of the measuring and sampling system shown in FIG. 3.

FIG. 3a is a diagrammatic view of a prototype implementation of the amplifier 24 shown in FIG. 3. The prototype implementation basically comprises a cascade two-stage amplifier circuit comprising two inverting amplifier stages implemented by means of a dual JFET operational amplifier of the type TL072 which is commercially available from the company SGS. The electronic circuit was implemented by means of the following components:

R1: 301 kΩ resistor,
R2: 1 kΩ resistor,
R3: 10 kΩ resistor,
R4: 2.05 kΩ resistor,
R5: 10 kΩ variable resistor or linear potentiometer,
R6: 2.05 kΩ resistor,
C1: 1 μF condenser,
IC1, IC2, TL072.

Figure 3B:
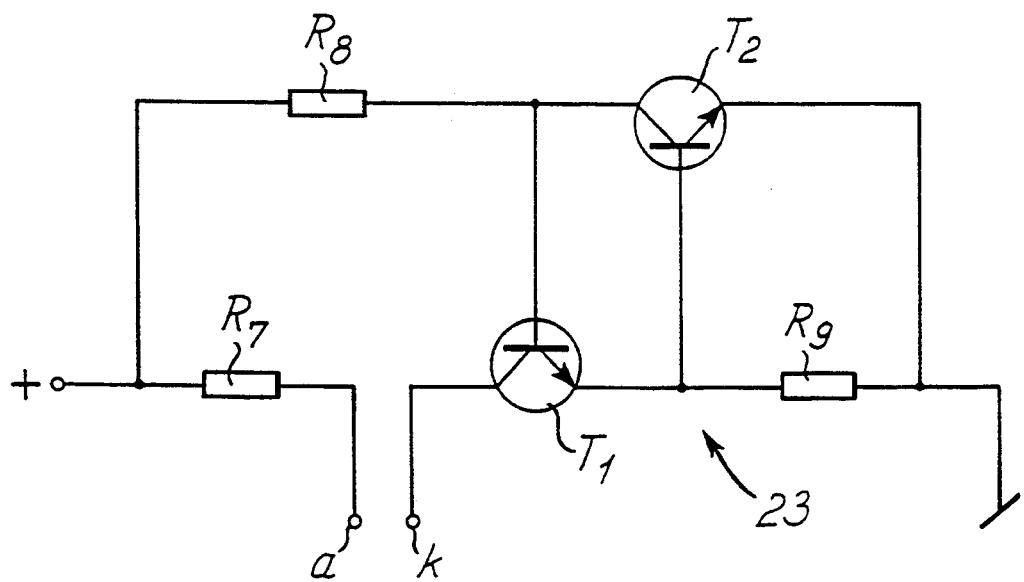
FIG. 3b is a detailed diagrammatic view of a presently preferred implementation or embodiment of a power source constituting a component of the prototype implementation of the measuring and sampling system shown in FIG. 3.

In FIG. 3b, a diagrammatic view of the power source or current generator 23 is shown. The power source basically comprises a current source implemented by means of an emitter-grounded NPN transistor T1, the collector of which is connected to the cathode k of the LED 1, the anode a of which LED is connected to a positive supply voltage loaded through a current-limiting resistor R7. The emitter of the emitter-grounded NPN transistor T1 is connected to the basis of a current-limiting NPN transistor T2, the emitter of which is grounded, and further connected to ground through an emitter resistor R9. The basis of the transistor T1 is connected to the collector of the transistor T2 and is further connected through a resistor R8 to the positive supply voltage. The power source was implemented by means of the following components:

R7: 100 Ω resistor,
R8: 10 kΩ resistor,
R9: 30 Ω resistor, and
T1 and T2: BC546 NPN transistors.

FIG. 4 is a perspective view of the degasser 22. The degasser comprises a closed vessel 30 (in a preferred embodiment made of stainless steel, although other sufficiently strong and vacuum-tight materials such as glass and certain plastics may equally well be employed) kept under vacuum by means of a suction device (not shown) connected via a conduit 31. A reagent solution to be degassed is passed, via a straight section 32 of a conduit 32/33 to the far end of the closed vessel, from which point a spiralling coiled section 33 of the conduit 32/33 extends back to the opposite end of the closed vessel. The conduit 32/33 is made of gas-permeable silicone rubber tubing (which in a preferred embodiment has an inner diameter of 0.5 mm) which allows gas from the reagent solution passing through the conduit in the vacuum vessel 30 to be released from the solution by penetration through the wall of the silicone polymer conduit and into the vacuum vessel. The total length of the conduit 32/33 is 0.5 m.

Method of operation of the measuring device/system

The amplified voltage output from the photodiode is received and processed by the computer 26 and/or by the recorder 25. A logarithmic input connection of the recorder is used to obtain signals whose magnitude is proportional to the absorbance of the measured sample. When the computer is used for receiving and processing the amplified photodiode output, the absorbance of the liquid sample in the measuring chamber is calculated on the basis of a previously determined baseline. A VDU (Visual Display Unit; suitably a standard computer monitor) 27 is connected to the computer for visual display of the analytical results obtained according to the method of the invention.

The computer is programmed to perform the following sequence:

Period A: Reagent or reference solution is passed, by means of the pump, from the reservoir through the first conduit 6, the measuring chamber 4, the second conduit 8 and the filter 50 and into the liquid medium. The pump is operated at constant speed and in a constant direction of pumping. The duration of period A is denoted "washing time".

Period B: The amplified voltage output from the photodiode is recorded repeatedly. During these recordings, the pump operates as in period A. The average (mean) values of the recordings of period B give the baseline or reference level. The duration of period B is denoted "baseline time".

Period C (optional): The pump is at a standstill. The duration of period C is denoted "pause time".

Period D: The direction of pumping is reversed and the pump is started, whereby liquid medium is drawn through the second conduit and into the flow cell (measuring chamber). The pump runs for a preselected period of time, denoted "sample time", whereafter it is stopped. During the sample time, the amplified voltage output from the photodiode is measured. The absorbance is calculated on the basis of the latter values and the baseline or reference level established in period B, and corresponding values of absorbance and time containing the analytical information are plotted on the VDU. The total duration of period D is denoted "time of analysis".

EXAMPLE 2

Measurement of absorbance at a preselected wavelength

The purpose of the experiment was to verify the method of the present invention outlined above. The parameter measured in period D of the method (see Example 1) was the absorbance of the liquid medium, and the liquid medium and the analytical reagent or reference solution were chosen so that their absorbance was different.

The experiment was conducted using the equipment described in Example 1. The spectrophotometric measurement was carried out at a preselected wavelength of 560 nm, an LED emitting predominantly light of this wavelength having been chosen so as to give maximal absorbance values when monitoring the species of interest in the Examples given below.

In accordance with the method of the present invention, the following cycle was effected: By means of the pump, reference solution was passed from the reservoir through the first conduit, the flow cell (measuring chamber), the second conduit and the filter and into the liquid medium. The pump was operated at constant speed and in a constant direction during this "washing time" period. After this period, the voltage signal from the photodiode was sampled by the computer at 1/10 second intervals. During this period ("baseline time" period), the pump was operated as during the washing period. The average (mean) values of the sampled (and recorded) signals generated the baseline or reference level. The direction of pumping was then reversed and the pump was started again, whereby liquid medium was drawn through the second conduit and into the flow cell (measuring chamber). The pump was operated for a preselected period of time (the "sample time", cf. below). During this sample time, the amplified voltage output from the photodiode was measured.

The absorbance was calculated taking account of the established baseline or reference level, and corresponding values of absorbance and time were plotted on the VDU. The "time of analysis" in this case is equal to the sample time.

It should be noted here that it is in principle possible to measure the baseline level, if so desired, while the liquid medium is being transferred, by the pump, towards the measuring chamber. In this case it is, of course, a prerequisite that the liquid medium has not yet entered the measuring chamber.

Two runs were conducted in this experiment, having a total duration of 48 seconds and 171 seconds, respectively.

Table 1 summarizes the experimental conditions.

TABLE 1

| Measuring chamber: | i.d. (internal diameter) = 0.7 mm |
| --- | --- |
| | Optical path length = 11.4 mm |
| Pumping tube: | i.d. = 0.381 mm |
| Pumping rate/speed: | 30 rpm (all running periods) |
| Washing time: | 27 sec. and 120 sec., respectively |
| Baseline time: | 1 sec. |
| Pause time: | 0 sec. |
| Sample time: | 10 sec. and 25 sec., respectively |
| Time of analysis: | 10 sec. and 25 sec., respectively |
| Liquid medium: | Solutions of $KMnO_4$ in water |
| Reference solution: | Water |

The variation of the measured absorbance versus time based on the voltage output signals read from the pen recorder is illustrated in FIG. 5a. The analytical information is obtained in the period denoted D, which corresponds to the "time of analysis" (see FIG. 5b). The maximum absorbance value is used as a measure for the absorbance of the liquid medium.

Figure 5C:
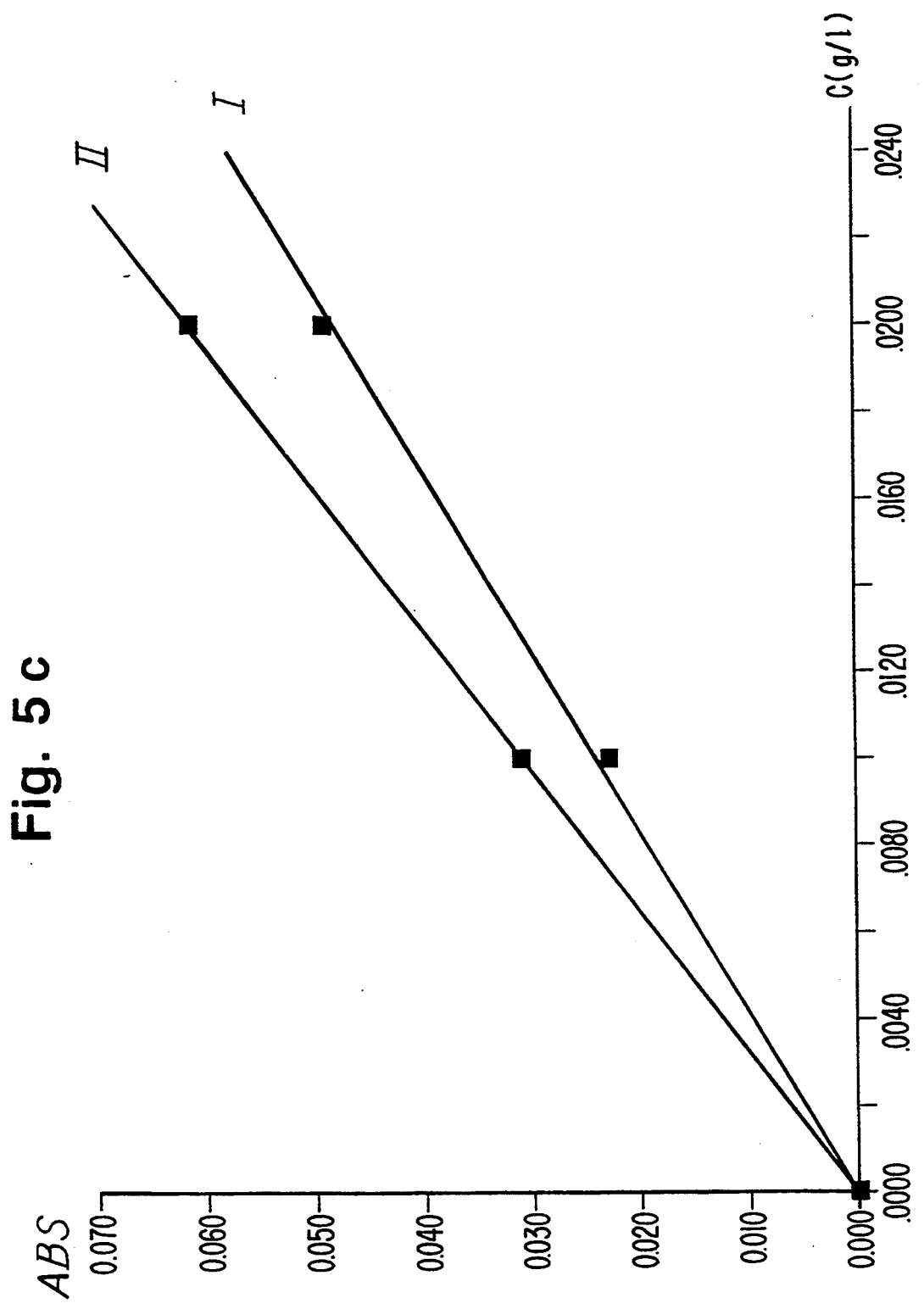
FIG. 5c is a plot of absorbance at the end of period D (vertical axis) versus concentration in g/l (horizontal axis) (see Example 2).

By increasing the sample time, the sensitivity of the absorbance measurement can be increased. This is illustrated in FIG. 5c, which shows the measured absorbance versus concentration (in g/l) for two different tests with sample times of 10 seconds (I) and 25 seconds (II), respectively.

EXAMPLE 3

Influence of matrix effect(s) [ghosting error(s)] on signals—measurement of index of refraction The purpose of the experiment was to investigate the influence of differences in the refractive index of the analytical reagent or reference solution and of the liquid medium in question on the signals recorded (the measurements) according to the method of the invention, i.e. the influence of the optical phenomenon "matrix effect" or "ghosting error" on the analytical results obtained.

The parameter measured in period D of the method was the absorbance of the liquid medium, and the liquid medium and the analytical reagent or reference solution were chosen so that their refractive indexes were different.

The experiment was carried out in a manner analogous to that described for Example 2, with the exception that the pump was stopped for a preselected period of time (the "pause time") after the establishment of the baseline/reference level, and that the sample time differed from the time of analysis.

Four test runs were conducted in this experiment. The liquid media were aqueous solutions of sodium chloride (10 g/l, 15 g/l, and 30 g/l) and a mixture of ethanol and water (8% w/w ethanol), respectively, and the reference solution was water.

Table 2 summarizes the experimental conditions.

TABLE 2

| Measuring chamber: | i.d. (internal diameter) = 0.8 mm |
| --- | --- |
| | Optical path length = 6.0 mm |
| Pumping tube: | i.d. = 0.190 mm |
| Pumping rate/speed: | Period A and B: 45 rpm |
| | Period D: 18 rpm |
| Washing time: | 10 sec. |
| Baseline time: | 1 sec. |
| Pause time: | 10 sec. |
| Sample time: | 3.5 sec. |
| Time of analysis: | 25 sec. |
| Liquid media: | Solution of NaCl in water (10 g/l); |
| | Solution of NaCl in water (15 g/l); |
| | Solution of NaCl in water (30 g/l); |
| | Ethanol in water (8% w/w ethanol); |
| Reference solution: | Water |

Figure 6:
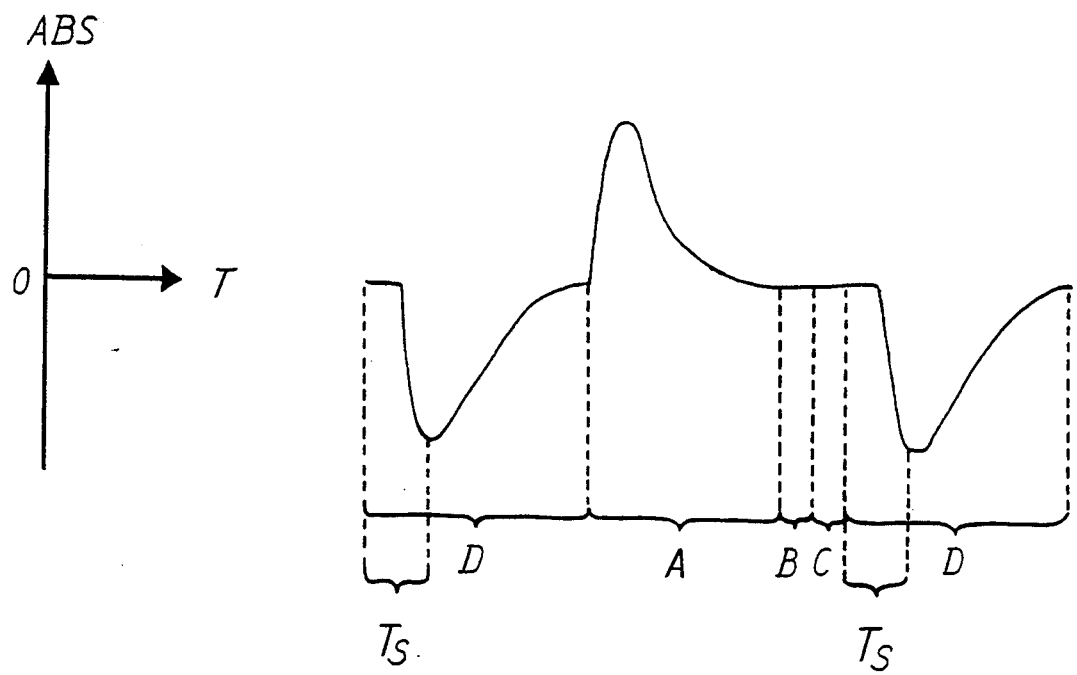
FIG. 6a is a graphical representation (vertical axis: absorbance; horizontal axis: time) of RFA signals obtained when the sample and analytical reagent/reference solution differ only in refractive index (see Example 3). The sample time is indicated by the symbol $T_S$.
FIG. 6b is a graphical representation (vertical axis: absorbance; horizontal axis: time) of RFA signals from period D containing the analytical information (see Example 3).
FIG. 6c is a plot of absorbance (vertical axis) versus index of refraction increment above the index of refraction of pure water (horizontal axis) for sodium chloride solutions and for an ethanol/water mixture (see Example 3). The curve is drawn through the data points for pure water and for the sodium chloride solutions (indicated by black square symbols); the data point for the ethanol/water mixture is indicated by a black diamond-shaped symbol.
Figure 6:
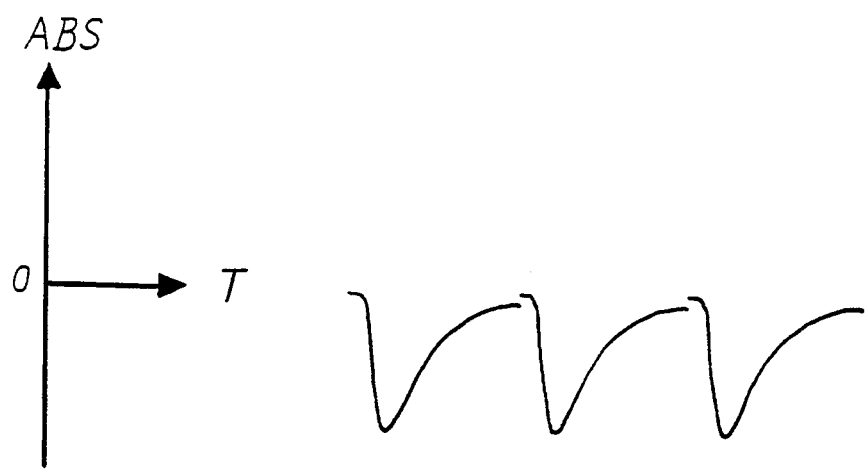

The variation of the measured absorbance versus time based on the output signals from the pen recorder is illustrated in FIG. 6a. The analytical information is obtained in the period denoted D which corresponds to the "time of analysis".

FIG. 6b shows a number of signals recorded for period D. Since neither water nor any of the components present in the sample solutions exhibit any appreciable absorption bands around 560 nm, it is clear from FIGS. 6a and 6b that:

(i) a difference in the refractive indexes of the sample and reference solutions leads to an "absorbance" signal. The minimum (extremum) value of the absorbance in the absorbance vs. time plot (FIG. 6b) can be taken as a measure of this refractive index difference;

(ii) the absorbance signal arising from the difference in refractive index decays to zero after switching off the pump (i.e. the last part of period D).

Figure 6C:
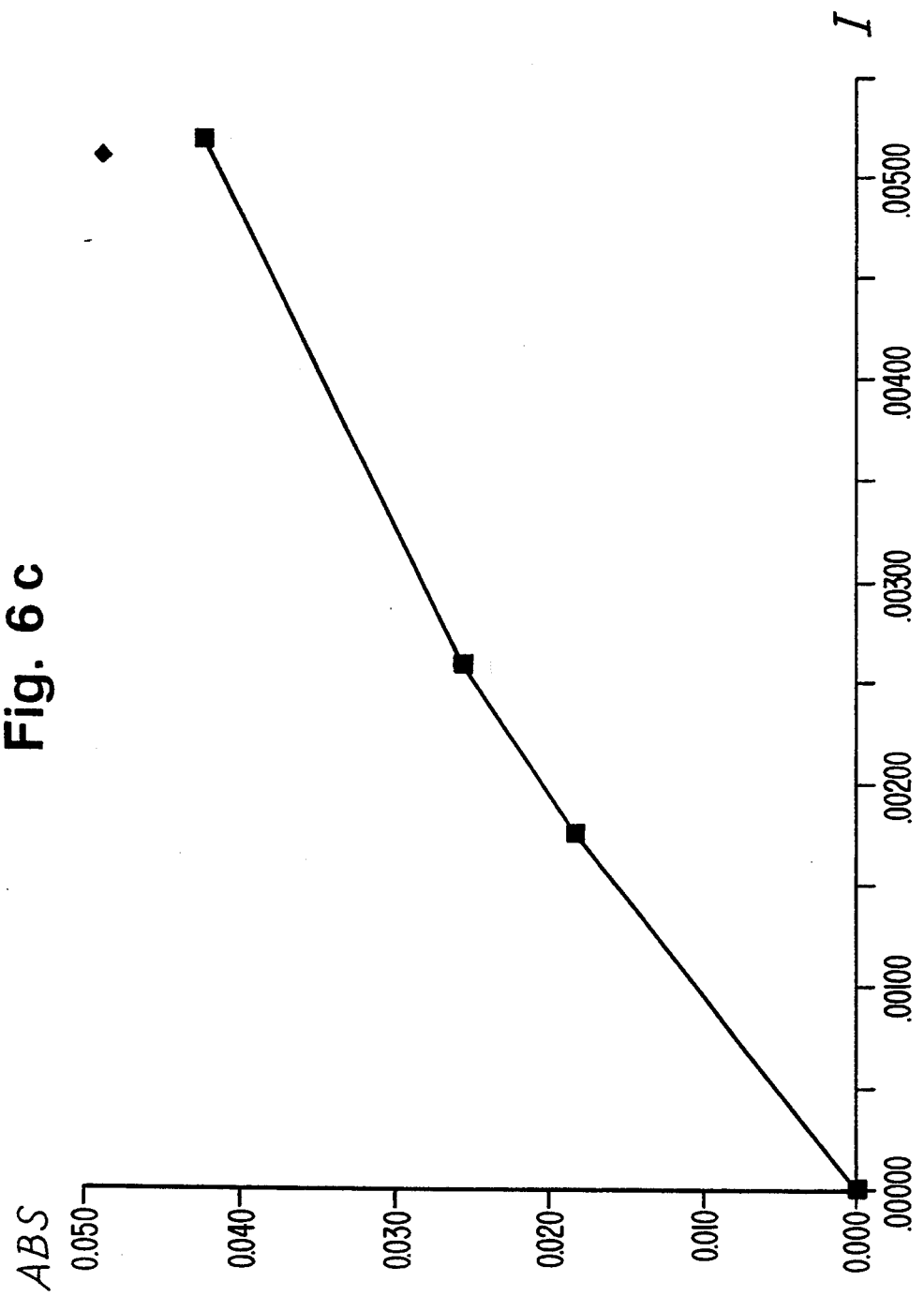

A plot of the extremum "absorbance" values vs. "index of refraction increment" (i.e. difference between solution refractive index and that of pure water) for the three NaCl solutions and for the ethanol/water mixture (see Table 2) (FIG. 6c) shows the smooth correlation between the two parameters [refractive index data taken from "Handbook of Chemistry and Physics", CRC Press 1974]. It is thus clearly possible, using the apparatus described here and within certain limits, to use this correlation to determine the refractive index of solutions of known composition.

EXAMPLE 4

Calibration of measuring device with bis(diazotized) 3,3'-dichlorobenzidine in a flow system Table 3 summarizes the experimental conditions.

TABLE 3

| Measuring chamber: | i.d. (internal diameter) = 0.8 mm |
| --- | --- |
| | Optical path length = 6.0 mm |
| Pumping tube: | i.d. = 0.190 mm |
| Pumping rate/speed: | Period A and B: 45 rpm |
| | Period D: 18 rpm |
| Washing time: | 10 sec. |
| Baseline time: | 1 sec. |
| Pause time: | 10 sec. |
| Sample time: | 2.0 sec. |
| Time of analysis: | 50 sec. |

TABLE 3-continued

| | |
|---|---|
| Liquid medium: | Various concentrations of bis(diazotized) 3,3'-dichlorobenzidine in a matrix of 3% (w/w) NaCl in 0.1M HCl. |
| Reference solution: | Chromotropic acid (4,5-dihydroxynaphthalene-2,7-disulfonic acid) (1.6 g/l) in a mixture of dimethylformamide and water (1:1, v/v) |

Figure 7:
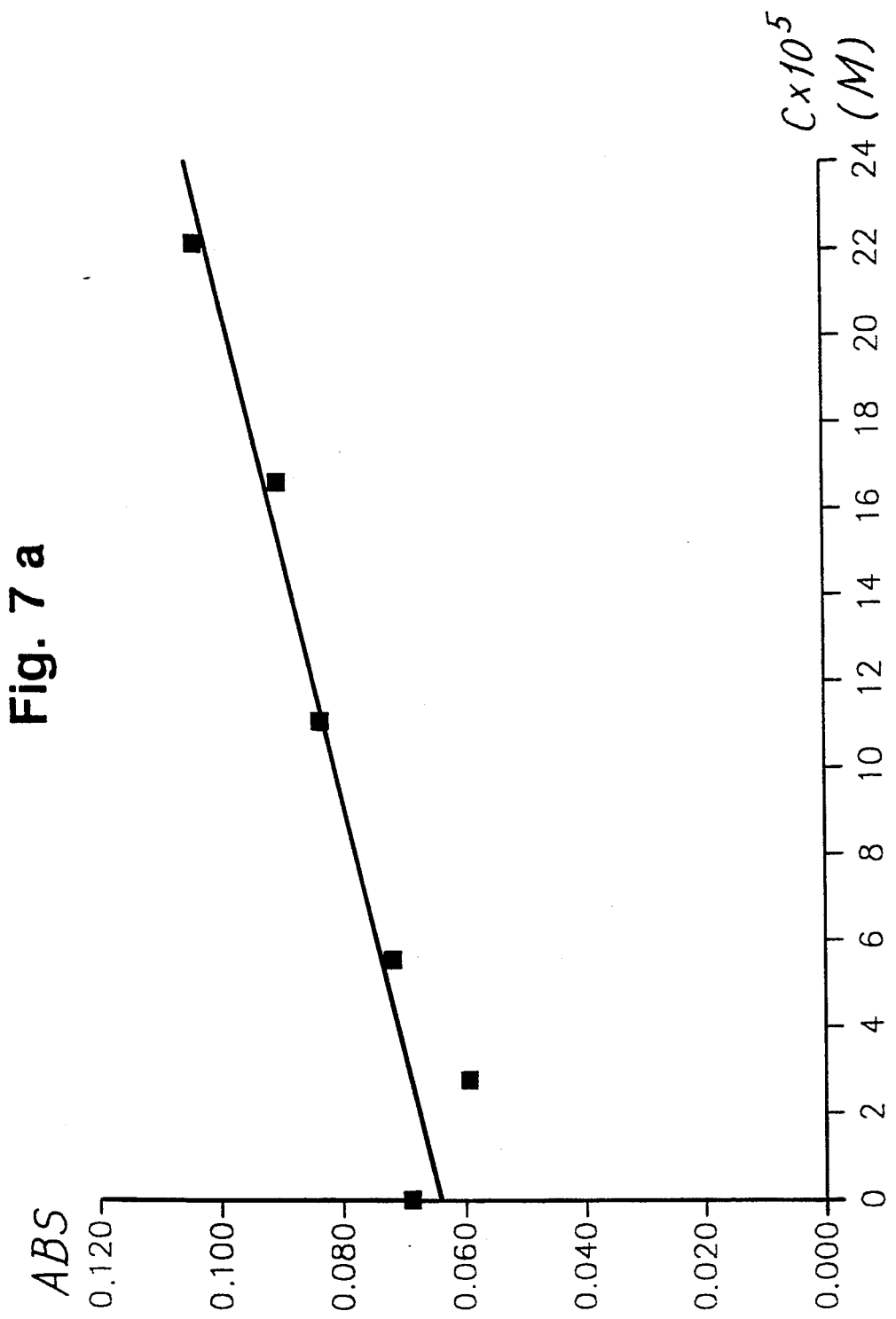
FIG. 7a is a plot (vertical axis: extremum value of absorbance in period D; horizontal axis: $10^5$ X concentration in mole/liter) for the calibration of a measuring device with bis(diazotized) 3,3'-dichlorobenzidine (see Example 4).
FIG. 7b is a plot (vertical axis: absorbance at the end of period D; horizontal axis: $10^5$ X concentration in moles/liter) for the calibration of the measuring device with bis(diazotized) 3,3'-dichlorobenzidine (see Example 4).
Figure 7B:
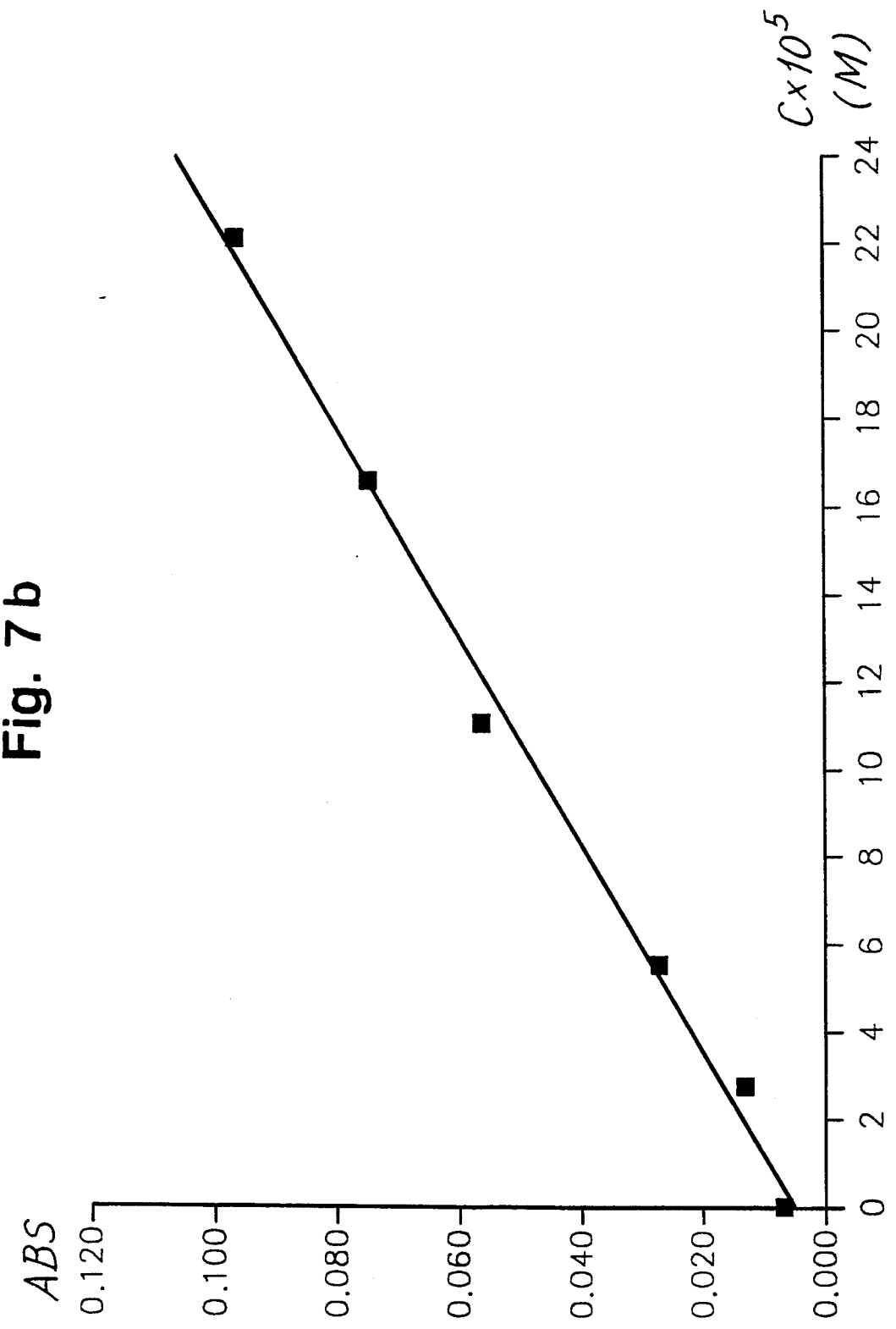

The measuring device was placed in a flowing stream of the liquid medium (flow rate 30 cm³/min.). FIG. 7a shows a calibration curve in which the extremum value of the absorbance in period D is taken as a measure of the concentration of bis(diazotized) 3,3'-dichlorobenzidine. As a result of the large differences in refractive index between sample and reagent/reference solutions, the sensitivity (slope) is poor, and large absorbance values are obtained for zero concentration of the bis(diazotized) 3,3'-dichlorobenzidine. In contrast, the calibration curve shown in FIG. 7b was obtained using the absorbance measured at the end of period D. This calibration curve shows satisfactory sensitivity (slope), and the absorbance measured at zero concentration of bis(diazotized) 3,3'-dichlorobenzidine deviates only very slightly from zero. This example thus shows how use of the stopped-flow technique eliminates or greatly reduces interference from the matrix effect.

EXAMPLE 5

Dependence of "time of analysis" on flow cell dimensions

The time required to achieve elimination of the matrix effect by use of stopped-flow technique is dependent inter alia on the diameter of the measuring chamber of the flow cell, as illustrated by the following example.

Table 4 summarizes the experimental conditions in question.

TABLE 4

| | |
|---|---|
| Measuring chamber: | i.d. = 0.5 mm ($d_1$) or 0.8 mm ($d_2$) Optical path length = 6.0 mm |
| Pumping tube: | i.d. = 0.190 mm |
| Pumping rate/speed: | 30 rpm (all periods) |
| Washing time: | 20 sec. |
| Baseline time: | 1 sec. |
| Pause time: | 0 sec. |
| Sample time: | 3.5 sec. |
| Time of analysis: | 30 sec. |
| Liquid medium: | Solution of NaCl in water (2.5% w/w) |
| Reference solution: | Water |

Figure 8:
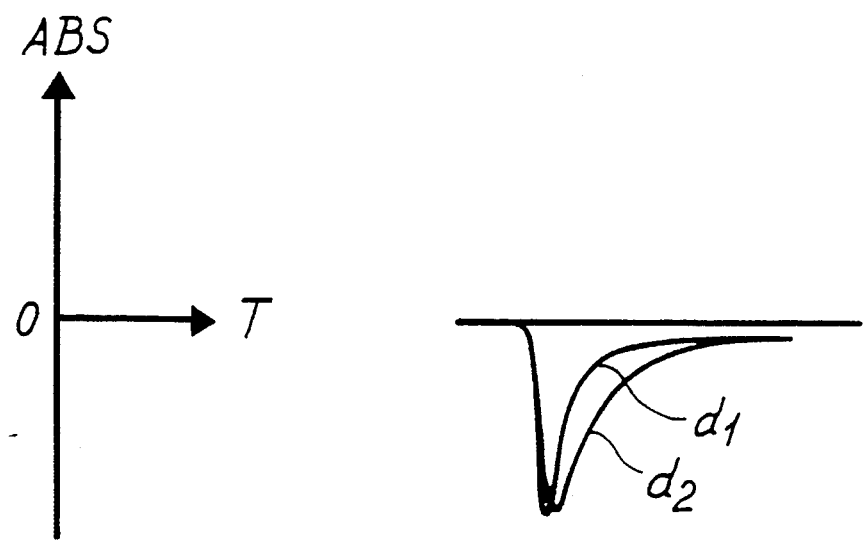
FIG. 8 is a graphical representation of the variation of absorbance (vertical axis) with time (horizontal axis) in period D observed using a 2.5% (w/w) aqueous sodium chloride solution as sample and pure water as reference solution in two flow cells differing only in internal diameter. 1 denotes an internal diameter of 0.5 mm, and 2 denotes an internal diameter of 0.8 mm (see Example 5).

The absorbance values measured in period D using the above two flow cells differing only with respect to the diameter of the measuring chamber are shown in FIG. 8. It is clear from this figure that the time required for elimination of the matrix effect is smallest for the flow cell having the measuring chamber of smallest diameter ($d_1$). Thus, in the design of a flow cell for use in Reversing Flow Analysis with stopped flow, it is desirable that the diameter of the measuring chamber is as small as possible. This will lead to small "times of analysis" which are a prerequisite for close to real-time monitoring and closed-loop control applications.

EXAMPLE 6

Monitoring of the diazonium salt concentration during the production of "Pigment Yellow 1" by a batch method The title pigment is produced by a batch method in which a solution of diazotized 2-nitro-4-methylaniline is added to a suspension of acetoacetanilide at a pH of 4–5 and a temperature of, normally, ca. 20° C. If the concentration of diazotized 2-nitro-4-methylaniline in the reaction vessel exceeds certain limits during the addition of the diazonium salt, the quality of the pigment produced is reduced owing to the formation of by-products via side reactions of the diazonium salt. Spot-test methods have traditionally often been used to check that the concentration of diazonium salt is below the desired limit. Reversing Flow Analysis combined with stopped flow provides the possibility of monitoring this process under conditions which are close to real-time conditions. The measuring device is immersed in the reaction medium in the reaction vessel. Table 5 summarizes the experimental measurement conditions.

TABLE 5

| | |
|---|---|
| Measuring chamber: | i.d. (internal diameter) = 0.5 mm Optical path length = 6.0 mm |
| Pumping tube: | i.d. = 0.190 mm |
| Pumping rate/speed: | Period A and B: 45 rpm Period D: 18 rpm |
| Washing time: | 10 sec. |
| Baseline time: | 1 sec. |
| Pause time: | 0 sec. |
| Sample time: | 3.5 sec. |
| Time of analysis: | 20 sec. |
| Reference solution: | Chromotropic acid (1.6 g/l) in a phosphate buffer of pH 10. |

FIG 9a shows a plot of the absorbance (vertical axis) measured at the end of period D versus time (horizontal axis). The individual measurements are joined by straight lines. These absorbance values are proportional to the concentration of the diazonium salt (see Example 4). Two parameters were varied during the addition of the diazonium salt solution to the reaction medium in the reaction vessel, viz. pH and the rate of addition.

Variation of pH in the reaction vessel pH was maintained constant by the addition of 2M NaOH solution. Addition of NaOH was temporarily halted for a period of time indicated by and bounded by the two vertical dotted lines in FIG. 9a. In the absence of NaOH, the pH in the reaction medium decreased as a result of H+ release during the coupling reaction and due to the acid present in the diazonium salt solution itself. The rate of the coupling reaction decreases with decreasing pH, resulting in a rise in the concentration of the free diazonium salt in the reaction medium. FIG. 9a shows the buildup in concentration of the free diazonium salts in the reaction medium. When the concentration of diazonium salt attained a level clearly detectable by a spot-test method (the approximate detection limit employing a spot-test method is indicated by a heavily drawn vertical bar on the absorbance axis of FIG. 9a), addition of the NaOH solution was continued. The figure shows how the concentration of free diazonium salt then rapidly decreased to a low level.

Variation in rate of addition of diazonium salt solution

The influence of variation in the rate of addition employed is depicted in FIG. 9b, which shows the relative rate of addition in per cent (vertical axis) versus time (horizontal axis). Addition of the diazonium salt solution was discontinued a number of times during the overall process time. As can be seen from the figure, this immediately resulted in a fall in absorbance to a value of essentially zero.

Optimization

When optimizing a batch production of pigments, two factors are of major importance:

1) The degree of conversion of the coupling component in question must be as close to 100% as possible, and at the same time the concentration of the free diazonium salt should be kept at a minimum to avoid the formation of undesired by-products;

2) The requirements of a satisfactory high capacity for each production unit necessitates the minimization of the overall process time.

The use of Reversing Flow Analysis combined with stopped-flow allows the optimization which is necessary to fulfil these requirements to be performed on-line. As can be seen from FIGS. 9a and b, an increase in the rate of addition of the diazonium salt solution halfway through the overall process resulted only in a minute increase in the free concentration of this species in the reaction medium. Thus, closed-loop control of the rate of addition on the basis of Reversing Flow Analysis measurement of the diazonium salt concentration will permit a higher rate of addition, thus reducing the overall process time.

The termination of a batch process is often a critical stage in the process. The concentration of the coupling component starts to decrease as the amount of solid-phase coupling component diminishes (only relatively large crystals of the coupling component remain at this stage, resulting in a decrease in the rate of dissolution as a result of the decrease in surface area/volume ratio for large crystals relative to smaller crystals). FIG. 9a shows the response of the detector to this situation (this stage is indicated by III in FIG. 9a. A concomitant increase in the free concentration of the diazonium salt in the reaction medium thus took place and could only be kept to a minimum by decreasing the rate of addition of the diazonium salt solution. The addition of diazonium salt solution was eventually discontinued. Upon resuming the addition, much higher free concentrations of the diazonium salt resulted, and were detectable by a traditional spot-test method (corresponding to the stage indicated by IV in FIG. 9a). Thus, closed-loop control of the rate of addition of the diazonium salt solution also facilitates optimization of the degree of conversion of the coupling component without the attendant formation of undesired by-products.

The importance of eliminating matrix effects

Figure 9D:
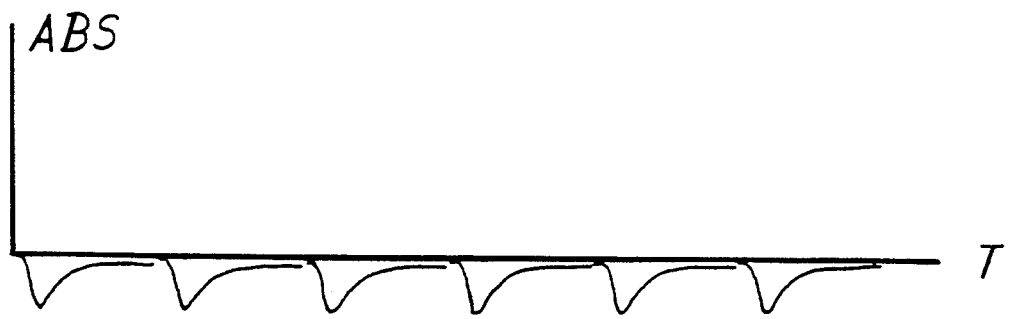
FIG. 9d is a graphical representation (vertical axis: absorbance; horizontal axis: time) of signals from period D obtained by sampling from the reaction vessel before the addition of the diazonium salt solution is initiated (see Example 6).
Figure 9E:
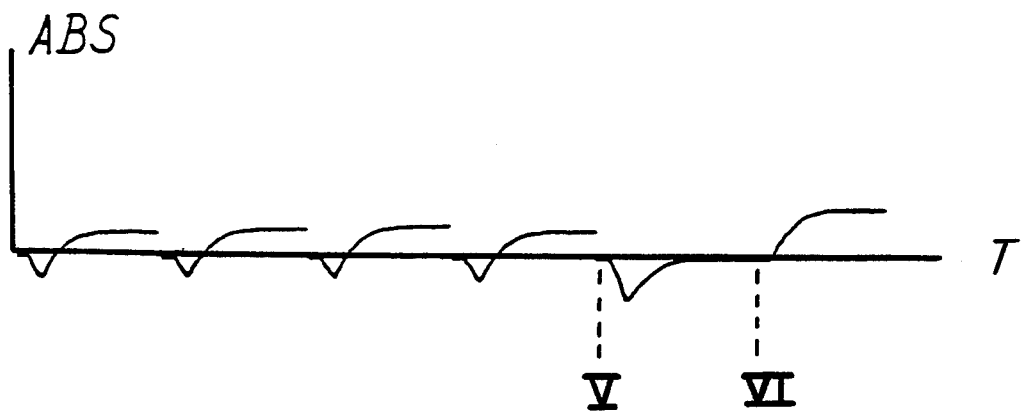
FIG. 9e is a graphical representation (vertical axis: absorbance; horizontal axis: time) of signals from period D obtained by sampling from the reaction vessel during the addition of the diazonium salt solution. The numbers V and VI indicate that the addition was discontinued and resumed, respectively (see Example 6).
Figure 9F:
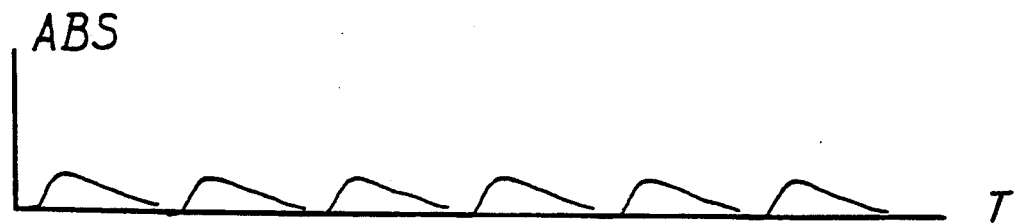
FIG. 9f is a graphical representation (vertical axis: absorbance; horizontal axis: time) of signals from period D obtained by sampling from the reaction vessel after termination of the process (see Example 6).

Processes taking place in a batch process, such as a batch-wise pigment producion process of the type described here, often result in a continuous change in the matrix. In the production of pigments the control of pH by the addition of NaOH results in the formation of sodium chloride. Depending upon the volume change during the reaction, this can result in either increasing, constant or decreasing concentrations of NaCl. It is thus impossible to correct for the matrix effect using a calibration procedure. The experiment described above provides an example of changes in the matrix effect which take place. FIGS. 9d-9f show signals measured in period D: FIG. 9d shows the signals obtained before the addition of diazonium salt is initiated; the difference in refractive index between the sample and the reagent solutions results in negative "absorbance" values. FIG. 9e shows signals recorded during the initial addition of a diazonium salt solution; the positive "absorbance" at the end of period D is a measure of the diazonium salt concentration in the reaction vessel. Upon discontinuing the addition of the diazonium salt solution, the signal reverted to that observed before starting the addition. Finally, FIG 9f shows signals recorded after termination of the process. The change in form of the signals seen in these three figures illustrates the change in matrix occurring during the process. It is thus clear that there is no straightforward way of taking account of these changes in the matrix by calibration procedures, since this would require continuing recalibration against standards whose matrix matches that of the reaction medium at any given stage in the process.

Checking of the baseline

FIG. 9c shows the relative variation in the baseline (vertical axis) versus time (horizontal axis) during the above-described experiment. As seen, the baseline is reasonably constant during the experiment. Measurement of the baseline level before each absorbance measurement is an important feature of Reversing Flow Analysis. This repeated measurement is known as the "modulation principle", and is also known from FIA. The modulation principle ensures that an increase in the concentration-dependent signal (e.g. absorbance) actually is the result of an increase in the concentration and not merely the result of a displacement of the baseline level. Repeated measurement of the baseline permits on-line checking of the sampling device, in that large and sudden changes in the signal indicate a defect in the device.

EXAMPLE 7

Monitoring of the bis(diazonium) salt concentration during the production of "Pigment Yellow 13" by a batch method Pigment Yellow 13 is produced by a batch method in which a solution of bis(diazotized) 3,3'-dichlorobenzidine is added to a suspension to 2,4-dimethylacetoacetanilide at a pH of 4–5 and at a temperature in the range 0°–50° C. As in Example 6, the quality of the pigment produced is lowered if the concentration of the bis(diazonium) salt exceeds certain limits.

Application of RFA combined with stopped-flow allows near real-time monitoring of the process. In the case of the present example, however, the greater molecular size of the azo compound formed in the analytical reaction between bis(diazotized) 3,3'-dichlorobenzidine and the analytical coupling component, viz. 4,5-dihydroxynaphthalene 2,7-disulfonic acid (chromotropic acid; CTA) renders the phosphate buffer employed in Example 6 inadequate as solvent. The azo compound formed in the analytical reaction tends to precipitate on the inside of the flow cell. This problem was therefore overcome by employing a 1:1 v/v mixture of water and N,N-dimethylformamide as solvent for the preparation of the reagent solution. Table 6 summarizes the experimental conditions.

TABLE 6

| | |
|---|---|
| Measuring chamber: | i.d. (internal diameter) = 0.8 mm |
| | Optical path length = 6.0 mm |
| Pumping tube: | i.d. = 0.190 mm |
| Pumping rate/speed: | Period A and B: 45 rpm |
| | Period D: 18 rpm |
| Washing time: | 15 sec. |
| Baseline time: | 1 sec. |
| Pause time: | 0 sec. |
| Sample time: | 2.0 sec. |
| Time of analysis: | 50 sec. |
| Reference solution: | Chromotropic acid (1.6 g/l) in a mixture of water and N,N-dimethylformamide (1:1, v/v) |

Figure 10A:
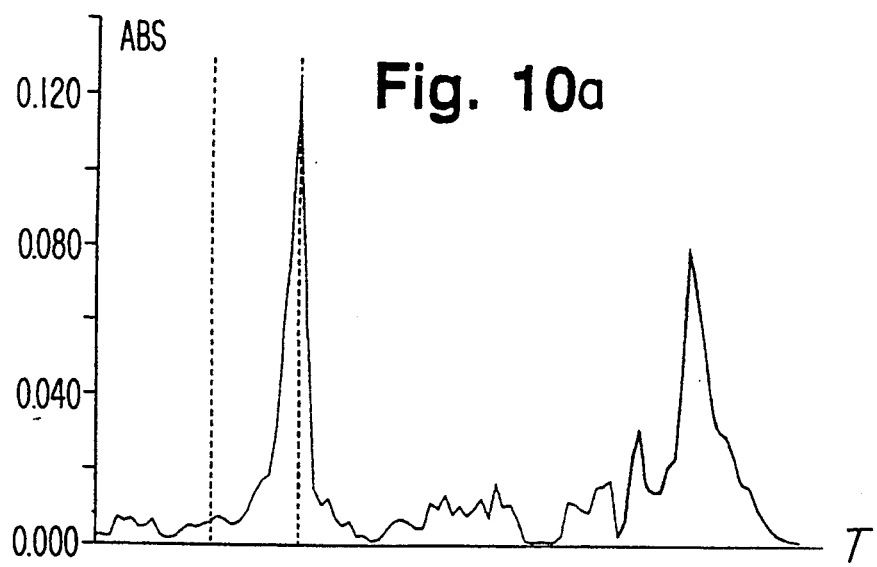
FIG. 10a is a graphical representation (vertical axis: absorbance; horizontal axis: time) of the data from the monitoring of the bis(diazonium) salt concentration during the production of Pigment Yellow 13 (see Example 7).
Figure 10B:
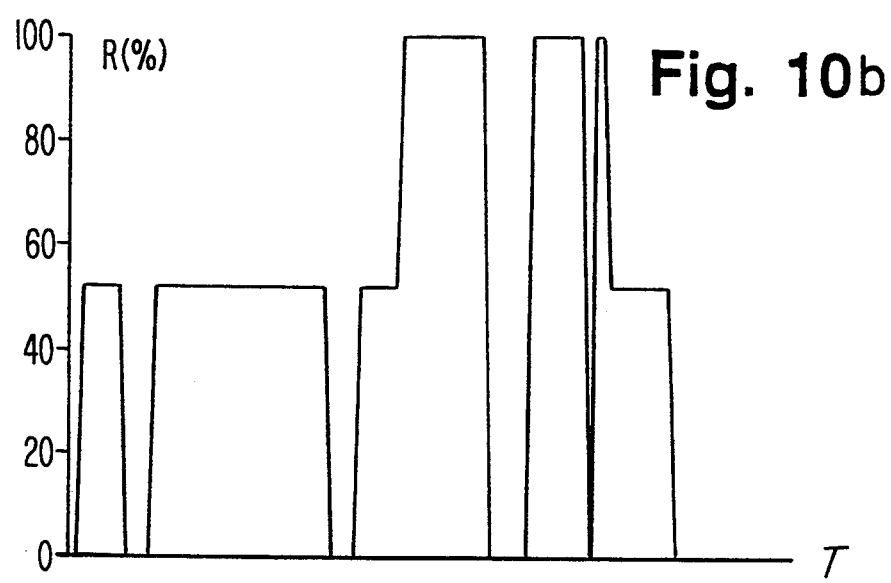
FIG. 10 is a graphical representation of data from the monitoring of the bis(diazonium) salt concentration during the production of Pigment Yellow 13 (see Example 7).
Figure 10C:
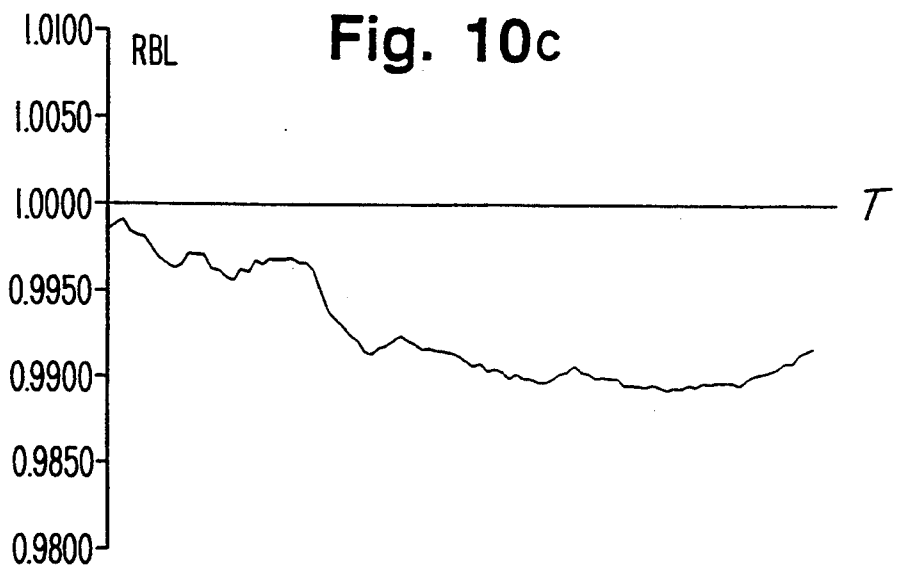

FIG. 10a depicts the absorbance measured at the end of period D (vertical axis) as a function of time (horizontal axis). The individual absorbance measurements, proportional to the concentrations of the bis(diazonium) salt in the reaction vessel, are joined by straight lines. The variation in process parameters [rate of addition (see FIG. 10c) and pH], in a manner similar to that described in Example 6, during the addition of the bis(diazonium) salt solution again illustrates the applicability of RFA combined with stopped flow in closed-loop control of the rate of addition and on-line optimization of the process as a whole. The small relative variation in the baseline (vertical axis) with time (horizontal axis) seen in FIG. 10c shows that the use of N,N-dimethylformamide does indeed prevent precipitation of the azo compound formed in the analytical reaction.

EXAMPLE 8

Monitoring of the glucose concentration in a fermentor

The concentration of glucose can be measured spectrophotometrically:

Glucose oxidase (GOD) catalyses the oxidation of β-glucose, with simultaneous reduction of the co-enzyme FAD to $FADH_2$:

β-glucose + FAD $\xrightarrow{GOD}$ D-glucono-δ-lactone + $FADH_2$

D-glucono-δ-lactone is irreversibly oxidized to gluconic acid and the $FADH_2$ is oxidized by oxygen with the reformation of FAD:

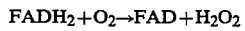

$FADH_2 + O_2 \rightarrow FAD + H_2O_2$

Provided sufficient oxygen is present, the amount of $H_2O_2$ formed is proportional to the amount of glucose present in the sample.

$H_2O_2$ can be detected spectrophotometrically as follows: A peroxidase enzyme (POD) such as horseradish peroxidase catalyses the oxidation of the product formed by coupling between 4-amino-1,2-dihydro-1,5-dimethyl-2-phenyl-3H-pyrazole-3-one (4-AP) and chromotropic acid to give a highly coloured product with an absorption maximum at 600 nm. The rate of this oxidation reaction is rather low and can be enhanced by the addition of 2,4-dichlorophenol. An RFA system for monitoring the reaction is shown schematically in FIG. 11. The measuring device 16 (comprising a measuring cell) is placed inside a fermentor 100, where it can be sterilized by steam. The three reagent reservoirs 20a, 20b and 20c shown in FIG. 11 contain the following reagents:

Reservoir 20a: A mixture of GOD and POD
Reservoir 20b: A solution of 4-AP, CTA and 2,4-dichlorophenyl
Reservoir 20c: Sodium hydroxide solution Upon mixing these solutions, a reagent solution with pH 10 is obtained. The high pH in the reagent solution serves as a sterilizing barrier between the fermentor and the surroundings.

Three pumps 21a, 21b and 21c connected to the reagent reservoirs operate with a three-way valve 101 open in periods A and B. Sampling is carried out by switching the valve, and a fourth pump 21d operates during the sample time of period D. A mixing coil 102 is positioned between the pumps 21a, 21b and 21c and the three-way valve 101.

EXAMPLE 9

In vivo application to living organisms

It is contemplated that the method of the invention can be used for chemical analysis in vivo in living organisms including humans and animals. In this embodiment of the invention, a compact measuring device comprising a measuring cell with a measuring chamber and forming part of a system of the invention is placed in situ in the organism [using state-of-the-art methodology it is possible to manufacture very small (e.g. of the order of size of that of an electronic chip) measuring devices of a type suitable for this purpose].

By means of optical fibres or other means for signal transmission, the measuring device is connected to a controlling computer, which may be portable or stationary, and narrow tubes connect the measuring chamber and the dosage aggregate (reservoir containing analytical reagent or reference solution).

Accordingly, the method and the system of the invention can be used for detecting at which point of time after their administration to the living organism in question, and for monitoring in which concentration, medicaments actually are located in the region where they are intended to perform their therapeutic activity. This will make it possible to control the administration of medicaments so as to secure a preselected, substantially optimum, activity of the medicament in the desired region of performance. Furthermore, a desired escalation, scaling-down or phasing-out of the administered dosage of medicament can be controlled.

At hospitals, monitoring of patients can take place by means of a central computer. Alternatively, the patients can remain at home while being in communication with the central computer at the hospital by means of a modem. Accordingly, the attending physician at the hospital can alter the prescribed dosage of medicament without requiring the presence of the patient. In the case of a portable system comprising the controlling computer and the dosage aggregate, this system can remain in radio contact with the mentioned central computer.

During surgical operations, the method and the analysis system of the invention can be used for on-line monitoring of the patient's condition.

In the field of diabetes, it is contemplated that the blood glucose level can be monitored regularly or continuously by means of the method and the analysis system of the invention, and this will then form the basis for an adjustment of the administered dosage of insulin. Such a glucose sensor would facilitate the medication of the ever increasing number of diabetics throughout the world.

In the clinical use as described above, it may in some cases be disadvantageous to admit reagent or reference solution into the living organism. Therefore, with reference to FIG. 12, in another embodiment of the invention it is contemplated that the sample and the reagent or reference solution can be disposed of by letting it return from the measuring cell 40 and into a receiving vessel (not shown) placed outside the organism. This can be accomplished by placing a valve 41, preferably a sterile one-way valve, or any device performing the same function, just behind an optical filter 42 in the second conduit 43, which valve prevents return of the liquid in the second conduit and the measuring chamber into the organism, and by establishing a third conduit 44 connecting the second conduit and a receiving vessel for disposal of the analysed sample and spent analytical reagent or reference solution, another valve 45, preferably a one-way valve, or any device performing the same function, being placed at the junction of the second and the third conduits. Optical fibres 46 connect the measuring cell and the computer/recorder (not shown), and a first conduit 47 connects the reservoir containing analytical reagent or reference solution (not shown).

Thus, in step (iii) of the method of the invention, the valve 41 at the junction of the filter and the second conduit is open, and the valve 45 at the junction of the second and the third conduit is closed. In steps (i), (ii) and (v) of the method of the invention, the valve 41 is preferably closed and the valve 45 at the third conduit is preferably open.

We claim:

1. An apparatus for quantitatively monitoring a chemical component dissolved in a liquid medium, comprising:
    a measuring cell having a measuring chamber for measuring a measurement parameter, said chamber being configured to form an interface zone between said liquid medium and an analytical reagent or reference solution when said analytical reagent or reference solution and said liquid medium are introduced into said measuring chamber, wherein said interface zone is suitable for measuring a value of said measurement parameter, said value of said parameter being a function of the amount of said chemical component present in said liquid medium;
    a reservoir containing said analytical reagent or reference solution;
    means for transferring liquid between said chamber and said reservoir, said means comprising a first conduit connecting said reservoir and said measuring chamber; and
    means for measuring said measurement parameter.

2. The apparatus of claim 1, further comprising a second conduit equipped with filter means for retaining suspended solids present in said liquid medium and connecting said measuring chamber and a source of said liquid medium.

3. An apparatus for on-line optimization and control of synthesis of azo compounds, wherein a reactant of a coupling reaction taking place in a liquid chemical reaction medium is quantitatively monitored, said apparatus comprising:
    (A) a measuring cell having a measuring chamber which is configured so that an interface zone is formed within said chamber between said liquid medium and an analytical reagent solution containing an analytical reagent when said analytical reagent solution and said liquid medium are introduced into said measuring chamber by the sequence of operations defined in steps (i) and (iii) below,
    said analytical reagent being such that it reacts with said reactant in solution to form a soluble, colored reaction product, and said measuring cell comprising
        (a) a light source from which a light beam is transmitted into said measuring chamber, and
        (b0 a detector which detects light from said light beam after said beam has passed into said interface zone in said measuring chamber;
    (B) a reservoir containing said analytical reagent solution; and
    (C) liquid transfer means capable of introducing one or both of said liquid medium and said analytical reagent solution into said measuring chamber,
    said apparatus being configured for performing a method comprising the steps of
        (i) charging said chamber with said analytical reagent solution by means of said liquid transfer means,
        (ii) measuring a reference or baseline value of the absorbance in said analytical reagent solution present in said measuring chamber by transmitting a light beam emitted from said light source through said reagent solution, said light beam eventually impinging upon said detector so as to generate a signal whose magnitude is related to the value of the absorbance in said analytical reagent solution,
        (iii) transferring said liquid medium into said measuring chamber by means of said liquid transfer means, thereby forming said interface zone between said liquid medium and said analytical reagent solution,
        (iv) measuring a measure of the absorbance of said soluble, colored reaction product formed in said interface zone by reaction of said reactant in solution with said analytical reagent in solution, by transmitting said light beam emitted from said light source through said liquid medium, said interface zone and said reagent solution present in said measuring chamber, said light beam being emitted in a direction substantially perpendicular to said interface zone and, after passing through said interface zone, said light beam impinging upon said detector so as to generate a signal whose magnitude is related to the value of the absorbance in said interface zone, said measurement optionally being preceded by a period of time after the formation of said interface zone, and
        (v) deriving a value for a measure of the concentration of said reactant in said chemical reaction medium on the basis of the measurements made in steps (ii) and (iv), and, in those cases where said value is outside preselected limits, regulating a process parameter or controlled variable so as to bring said value within said preselected limits.

4. The apparatus of claim 3, further comprising a first conduit connecting said reservoir and said measuring chamber; and a second conduit equipped with filter means for retaining suspended solids present in said liquid medium and connecting said measuring chamber and a source of said liquid medium.

5. The apparatus of claim 4, wherein said liquid transfer means is capable of transferring liquid in a first direction or in a second direction opposite to said first direction and is placed in connection with the first conduit.

6. The apparatus of claim 4, said liquid transfer means being placed in connection with the first conduit.

7. The apparatus of claim 3, wherein said light source comprises a light-emitting diode.

8. The apparatus of claim 3, wherein said detector comprises a photodiode.

9. The apparatus of claim 3, said measuring chamber being adapted for measurement of an optical or electrochemical measurement parameter.

10. The apparatus of claim 3, said measuring chamber being adapted for measurement of an optical parameter conventionally used in colorimetric, spectrophotometric, fluorimetric, phosphorimetric, turbidimetric/nephelometric or refractometric methods of analysis.

11. The apparatus of claim 3, said parameter being selected from the group consisting of transmitted light intensity, absorbance and refractive index.

12. The apparatus of claim 3, said measuring chamber being adapted for measurement of an electrochemical parameter conventionally used in potentiometric, conductimetric, amperometric, polarographic, voltammetric or coulometric methods of analysis.

13. The apparatus of claim 3, said parameter being selected from the group consisting of potential, current, resistance and conductivity.

14. The apparatus of claim 3, wherein said liquid medium comprises at least one dissolved chemical component and at least one solid chemical component of low solubility dispersed in the liquid medium, the dispersion optionally being achieved by the inclusion, in the liquid medium, of a dispersing agent.

15. The apparatus of claim 3, wherein the liquid forming the basis of said liquid medium is a liquid which does not react with any component dissolved or dispersed in said liquid medium.

16. The apparatus of claim 3, wherein the liquid forming the basis of said liquid medium is water.

17. The apparatus of claim 3, wherein the liquid forming the basis of said liquid medium is selected from the group consisting of aromatic hydrocarbons, chlorinated hydrocarbons, glycol ethers, nitriles, esters, alcohols, and dipolar aprotic solvents.

18. An apparatus according to claim 1 or 3, wherein said liquid medium is a medium in which is occurring a microbiological process for industrial use selected from the group consisting of fermentation processes and cell culture.

19. A method for on-line optimization and control of synthesis of azo compounds, said method utilizing the apparatus of claim 3, wherein a reactant of a coupling reaction between a coupling component and a diazonium compound taking place in a liquid chemical reaction medium is quantitatively monitored, said method comprising the steps of:
  (i) charging said chamber with said analytical reagent solution by means of said liquid transfer means,
  (ii) measuring a reference or baseline value of the absorbance in said analytical reagent solution present in said measuring chamber by transmitting a light beam emitted from said light source through said reagent solution, said light beam eventually impinging upon said detector so as to generate a signal whose magnitude is related to the value of the absorbance in said analytical reagent solution,
  (iii) transferring said liquid medium into said measuring chamber by means of said liquid transfer means, thereby forming said interface zone between said liquid medium and said analytical reagent solution,
  (iv) measuring a measure of the absorbance of said soluble, colored reaction product formed in said interface zone by reaction of said reactant in solution with said analytical reagent in solution, by transmitting said light beam emitted from said light source through said liquid medium, said interface zone and said reagent solution present in said measuring chamber, said light beam being emitted in a direction substantially perpendicular to said interface zone and, after passing through said interface zone, said light beam impinging upon said detector so as to generate a signal whose magnitude is related to the value of the absorbance in said interface zone, said measurement optionally being preceded by a period of time after the formation of said interface zone, and
  (v) deriving a value for a measure of the concentration of said reactant in said chemical reaction medium on the basis of the measurements made in steps (ii) and (iv), and, in those cases where said value is outside preselected limits, regulating a process parameter or controlled variable so as to bring said value within said preselected limits.

20. The method of claim 19, wherein said reactant of said coupling reaction is a diazonium salt, preferably a diazonium salt in solution or suspension.

21. The method of claim 19, wherein said reactant of said coupling reaction is a coupling component of an azo coupling reaction.

22. The method of claim 19, wherein said coupling reaction is carried out at a pH in the range of from 2 to 12, and at a temperature in the range of from $-5°$ to $99°$ C.

23. The method of claim 19, wherein the product of said coupling reaction is a yellow arylide or diarylide pigment and said coupling reaction is carried out at a substantially constant pH in the range of from 4 to 6.

24. The method of claim 19, wherein the coupling component in said coupling reaction is selected from the group consisting of: substituted and unsubstituted acetoacetanilides; N-phenyl-3-hydroxy-2-naphthalenecarboxamide (Naphthol-AS) and derivatives thereof; $\beta$-naphthol and substituted $\beta$-naphthols; $\beta$-oxo-naphthoic acid and substituted $\beta$-oxo-naphthoic acid; and 5-pyrazolone and substituted 5-pyrazolones; and the diazonium compound of the coupling reaction is obtained by diazotisation of an aromatic amine or diamine selected from the group consisting of: substituted anilines and substituted benzidines.

25. The method of claim 19, wherein said analytical reagent solution is an aqueous solution and comprises a buffer and/or an organic solvent.

26. The method of claim 19, wherein a diazonium reactant of a coupling reaction is monitored, and said analytical reagent solution comprises a coupling component bearing sulfonic acid, amino and/or hydroxy groups capable of ensuring adequate solubility of the azo colourant reaction product formed in the analytical reaction.

27. The method of claim 26, wherein the coupling component of said analytical reagent solution is selected from the group consisting of:
  7-hydroxy-1,3-naphthalenedisulfonic acid,
  1,8-dihydroxy-3,6-naphthalenedisulfonic acid and
  4-acetoacetylaminobenzenesulfonic acid.

28. The method of claim 19, wherein a coupling component of a coupling reaction is monitored, and said analytical reagent solution comprises a diazotised aromatic amine bearing sulfonic acid and/or hydroxy groups capable of ensuring adequate solubility of the azo colourant reaction product formed in the analytical reaction.

29. The method of claim 28, wherein said diazotised aromatic amine of said analytical reagent solution is selected from the group consisting of:
  diazotized 4-aminobenzenesulfonic acid,
  diazotized 3-amino-4-methoxybenzenesulfonic acid,
  diazotized 3-amino-6-methoxybenzene sulfonic acid and
  diazotized 2-amino-5-naphthalenesulfonic acid.

30. The method of claim 19, wherein said analytical reagent solution comprises ferric ions, and the coupling component of said coupling reaction is capable of forming light-absorbing complexes with the ferric ions.

31. The method of claim 30, wherein said coupling component is an unsubstituted or a substituted acetoacetanilide.

32. A method for quantitatively monitoring a chemical component dissolved in a liquid medium, said method comprising the steps of:
(i) charging, with said liquid medium and with an analytical reagent or reference solution, a measuring cell having a measuring chamber for measuring a measurement parameter, said chamber being configured to form an interface zone between said liquid medium and said analytical reagent or reference solution when said analytical reagent or reference solution and said liquid medium are introduced into said measuring cell, wherein an interface zone forms between said liquid medium and said analytical reagent or reference solution upon said charging; and,
(ii) measuring a value of a measurement parameter in said interface zone, said value being a function of the amount of said chemical component present in said liquid medium.

33. The method of claim 32, further comprising the step of measuring a reference or baseline value for said measurement parameter in said analytical reagent or reference solution.

34. A method according to claim 32, wherein a microbiological process for industrial use selected from the group consisting of fermentation processes and cell culture is taking place in said liquid medium.

35. The method of claim 32, wherein step (i) comprises
(a) initially charging said measuring chamber with said analytical reagent or reference solution, and
(b) measuring said measurement parameter to obtain a baseline or reference value thereof.

36. The method of claim 32, wherein the value of said measurement parameter is related directly to a product formed in said interface zone by reaction between said chemical component and a reactant present in said analytical reagent solution.

37. The method of claim 32, wherein the value of said measurement parameter is a function of the concentration of said chemical component present in said liquid medium.

38. The method of claim 32, wherein said measuring is preceded by a period of time after the formation of said interface zone.

39. The method of claim 32, further comprising the step of (iii) deriving the amount of said chemical component present in said liquid medium from the value obtained in step (ii).

40. The method of claim 32, wherein said measurement parameter is an optical or electrochemical parameter.

41. The method of claim 32, wherein said measurement parameter is an optical parameter conventionally used in colorimetric, spectrophotometric, fluorimetric, phosphorimetric, turbidimetric/nephelometric or refractometric methods of analysis.

42. The method of claim 32, wherein said measurement parameter is selected from the group consisting of transmitted light intensity, absorbance and refractive index.

43. The method of claim 32, wherein said measurement parameter is an electrochemical parameter conventionally used in potentiometric, conductimetric, amperometric, polarographic, voltammetric or coulometric methods of analysis.

44. The method of claim 32, wherein said measurement parameter is selected from the group consisting of electrical potential, current, resistance and conductivity.

45. The method of claim 32, wherein said measuring in step (ii) is preceded by a period of time required for the disappearance of any matrix effects or ghosting errors.

46. A method according to claim 32, wherein said liquid medium is a chemical reaction medium.

47. A method according to claim 32, wherein said liquid medium is a chemical reaction medium and comprises at least one dissolved chemical component and at least one solid chemical component of low solubility dispersed in the liquid medium, the dispersion optionally being achieved by the inclusion, in the liquid medium, of a dispersing agent.

48. A method according to claim 32, wherein said liquid medium is a chemical reaction medium and the liquid forming the basis of said liquid medium is a liquid which does not react with any component dissolved or dispersed in the liquid medium.

49. A method according to claim 32, wherein the liquid forming the basis of said liquid medium is water.

50. A method according to claim 32, wherein the liquid forming the basis of said liquid medium is selected from the group consisting of aromatic hydrocarbons, chlorinated hydrocarbons, glycol ethers, nitriles, esters, alcohols, and dipolar aprotic solvents.

51. A method according to claim 32, wherein the liquid medium is a chemical reaction medium, the chemical reaction being carried out in a continuous manner.

52. A method according to claim 32, wherein the liquid medium is a chemical reaction medium, the chemical reaction being carried out in a batch-wise manner.

53. A method according to claim 32, wherein the liquid medium is a chemical reaction medium, at least one reaction product of the chemical reaction being a solid which is slightly soluble or substantially insoluble in the liquid medium.

54. A method according to claim 53, wherein the at least one solid reaction product is a colourant.

55. A method according to claim 53, wherein the at least one solid reaction product is an azo compound.

56. The method of claim 32 wherein the results of the measurements made are used as a measured variable in an automation system for regulating one or more controlled variables of an industrial chemical process.

57. A method according to claim 56, wherein said automation system is a closed-loop control system.

58. A method according to claim 56, wherein said industrial chemical process is carried out in a continuous manner.

59. A method according to claim 56, wherein said industrial chemical process is carried out in a batch-wise manner.

60. A method according to claim 56, wherein said chemical process is operated in a continuous manner, and said one or more controlled variables of said automation system is/are selected from the group consisting of: flow rate of reactants and/or reaction products; temperature; pressure; pH; concentration of reactants, reaction products or by-products; and residence time.

61. A method according to claim 56, wherein said chemical process is operated batch-wise and said one or more controlled variables of said automation system is/are selected from the group consisting of: optimal process time; dosage rate of reactants; total amount of reactants added to the liquid medium; concentration of reactants, reaction products and by-products; volume; temperature; pressure; and pH.

62. A method according to claim 56, wherein said measurements are measurements of the concentration, or a quantity proportional thereto, of a chemical component present in said liquid medium.

63. A method according to claim 56, wherein a biological process for industrial use is taking place in said liquid medium.

64. A method according to claim 56, wherein a microbiological process for industrial use is taking place in said liquid medium.

* * * * *